United States Patent [19]

Lempert et al.

[11] Patent Number: 4,665,083

[45] Date of Patent: May 12, 1987

[54] IMINOTHIAZOLIDINE DERIVATIVES

[75] Inventors: Károly Lempert; Gyula Hornyák; Ferenc Bartha; Gabor Doleschall; József Fetter; József Nyitrai; Gyula Simig, all of Budapest; Károly Zauer, Szentendre; Peter Huszthy, Budapest; Antal Feller, Budapest; Lujza Petöcz, Budapest; Enikö Szirt, Budapest; Katalin Grasser, Budapest; Edit Berenyi, Budapest; Zsuzsanna Orr, Budapest; Etelka Pjeczka, Albertirsa, all of Hungary

[73] Assignee: Egis Gyogyszergyar, Budapest, Hungary

[21] Appl. No.: 726,867

[22] Filed: Apr. 25, 1985

[30] Foreign Application Priority Data

Apr. 25, 1984 [HU] Hungary ............... 1581/84

[51] Int. Cl.$^4$ ............. A61K 31/425; C07D 277/18
[52] U.S. Cl. ................... 514/370; 548/190; 548/193; 548/194
[58] Field of Search .......... 548/190, 193, 194; 514/370

[56] References Cited

U.S. PATENT DOCUMENTS

| | | | |
|---|---|---|---|
| 3,297,708 | 1/1967 | Garber et al. | 548/190 |
| 3,489,771 | 1/1970 | Donche et al. | 548/190 |
| 3,671,537 | 6/1972 | Toldy et al. | 548/193 |
| 3,775,425 | 11/1973 | Bosshard et al. | 548/190 |
| 3,898,340 | 8/1975 | Behner et al. | 514/370 |
| 4,029,803 | 6/1977 | Hunter et al. | 514/370 |

FOREIGN PATENT DOCUMENTS

| | | |
|---|---|---|
| 164034 | 4/1975 | Hungary . |
| 164035 | 4/1975 | Hungary . |
| 690238 | 4/1953 | United Kingdom . |

OTHER PUBLICATIONS

Acta Chimica Acadaemiae Scientiarum Hungaricae, Tomus 75, (2), pp. 99-110, (1973), NH Stretching Vibration Bands at Wavenumbers Lower Than 3000 $CM^{-1}$ VIII, Sohar et al.

Chem. Phar. Bull., 14(11), pp. 1201-1209, (1966), Hino et al., Radiation-protective Agents II., The Transformatin of 2-(2-Aminoethyl)thiopsudoureas to 2-amino-2-thiazolines.

Hino et al., Chem. Pharm. Bull., vol. 14, No. 11, pp. 1201-1209, (1966).

Sohar et al., Chemical Abstracts, vol. 78, No. 15: 96748j, (1973).

Primary Examiner—Donald G. Daus
Assistant Examiner—Stephen M. Kapner
Attorney, Agent, or Firm—Karl F. Ross; Herbert Dubno

[57] ABSTRACT

The invention relates to novel iminothiazolidine derivatives of the formula (I),

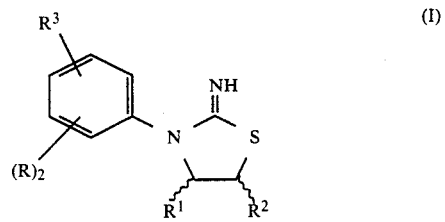

wherein
$R^1$ and $R^3$ represent, independently from each other, hydrogen or lower alkyl group,
$R^3$ is nitro or amino group,
R stands for halo, lower alkyl, haloalkyl, nitro, amino, hydroxy, lower alkoxy, carboxy or lower alkoxycarbonyl group, and
n is 0, 1 or 2, and pharmaceutically acceptable acid addition salts thereof.

The iminothiazolidine derivatives of the formula (I) possess valuable antidepressant, antiparkinsonic, antiepileptic and spasmolytic activities.

8 Claims, No Drawings

IMINOTHIAZOLIDINE DERIVATIVES

FIELD OF THE INVENTION

The invention relates to novel iminothiazolidine derivatives, a process for the preparation thereof and pharmaceutical compositions containing said iminothiazolidines.

BACKGROUND OF THE INVENTION

2-Imino-1-(o-nitrophenyl)-imidazolidines are described in the Hungarian patent specification No. 164,034. The Hungarian patent specification No. 164,035 refers to the synthesis of 2-imino-1-(o-aminophenyl)-imidazolidine derivatives. 2-Imino-3-(unsubstituted phenyl)-thiazolidine and the light protective effect of the latter compound have been described by Hino, T. et al. [Chem. Pharm. Bull. (Tokyo) 14 (11), 1201-1209 (1966)].

In particular, the invention relates to novel iminothiazolidine derivatives of the formula (I).

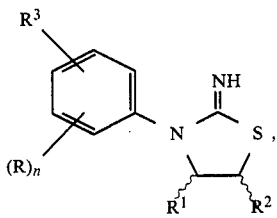

wherein
$R^1$ and $R^2$ represent, independently from each other, hydrogen or a lower alkyl group,
$R^3$ is nitro or amino group,
R stands for halo, lower alkyl, haloalkyl, nitro, amino, hydroxy, lower alkoxy, carboxy or lower alkoxycarbonyl, and
n is 0, 1 or 2,
and the pharmaceutically acceptable acid addition salts thereof.

In the specification a lower alkyl group is a linear or branch chained alkyl group having 1 to 4 carbon atoms, such as methyl, ethyl, n-propyl, isobutyl, etc. Halo means fluoro, chloro, bromo or iodo atoms. Haloalkyl comprises mono-, di- or trihaloalkyl groups, such as chloromethyl, bromomethyl, chloroethyl, dichloromethyl and especially trifluoromethyl. A lower alkoxy group is a linear or branch chained alkoxy having 1 to 4 carbon atoms, e.g. methoxy, ethoxy, n-propoxy, isobutoxy, etc. A lower alkoxycarbonyl group is, for example, methoxy- or ethoxycarbonyl, and can have 1 to 4 carbon atoms in the alkoxy chain.

The pharmaceutically acceptble acid addition salts of the iminothiazolidine derivatives of the formula (I) can be inorganic or organic acid addition salts, such as hydrochloride, hydrobromide, sulfate, nitrate, acetate, lactate, fumarate, maleate, tartrate, methanesulfonate, ethanesulfonate, etc.

A subclass of the compounds of the invention consists of the nitro compounds of the formula (Ia)

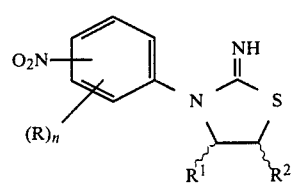

wherein $R^1$, $R^2$, R and n are as stated above, and the pharmaceutically acceptable acid addition salts thereof.

Preferred representatives of the nitro compounds of the formula (Ia) are derivatives in which the nitro group is in position 2 relative to the phenyl carbon atom bound to the thiazolidine nucleus.

Preferably, in formula (Ia) $R^1$ and $R^2$ are hydrogen, n is 0 or 1 and R represents chloro, trifluoromethyl, methoxy or amino group.

A further subclass of the compounds of the invention consists of the amino compounds of the formula (Ib)

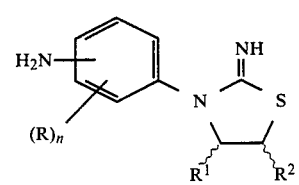

wherein $R^1$, $R^2$, R and n are as stated above, and the pharmaceutically acceptable acid addition salts thereof.

Preferred representatives of the amino compounds of the formula (Ib) are derivatives in which the amino group is in position 2 relative to the phenyl carbon atom bound to the thiazolidine nucleus.

Preferably, in formula (Ia), $R^1$ and $R^2$ stand for hydrogen or methyl, n is 0 or 1, and R represents a chloro, trifluoromethyl, methoxy or methyl group.

Especially preferred iminothiazolidine derivatives of the invention are:
3-(2-amino-4-chlorophenyl)-2-iminothiazolidine,
3-(2-amino-4-chlorophenyl)-2-imino-5-methylthiazolidine,
3-(2-amino-4-methylphenyl)-2-iminothiazolidine,
and the pharmaceutically acceptable acid addition salts thereof.

The novel iminothiazolidine derivatives of the invention have valuable antidepressant, antiparkinsonic, antiepileptic and spasmolytic properties.

The invention comprises all enantiomers, diastereomers and racemates of the compounds of the formula (I).

Furthermore, the invention relates to a process for preparing iminothiazolidine derivatives of the formula (I) and the pharmaceutically acceptable acid addition salts thereof, in which (a) for preparing compounds of the formula (I), wherein $R^3$ is nitro, i.e. compounds of the formula (Ia)

(a₁) an isothiocyanate of the formula (II)

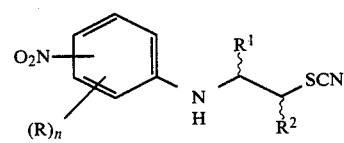

wherein $R^1$, $R^2$, R and n are as stated above, is cyclized in the presence of an acid; or (a₂) a compound of the formula (III)

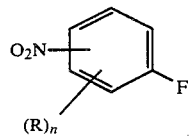
(III)

wherein R and n are as stated above, is reacted with a compound of the formula (IVa) or a tautomer of the formula (IVb)

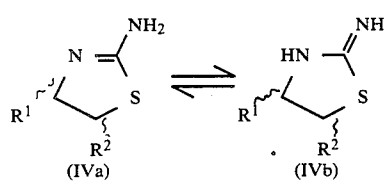

wherein $R^1$ and $R^2$ are as stated above; or (a₃) a compound of the formula (V)

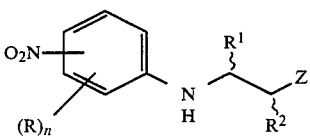
(V)

wherein $R^1$, $R^2$ and n are as stated above and Z is a leaving group, is reacted with thiourea, and the obtained compound of the formula (VI)

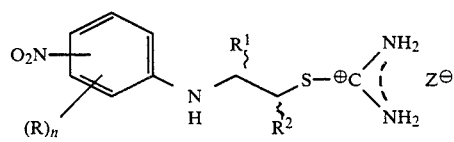
(VI)

is cyclized; or (a₄) a compound of the formula (VII)

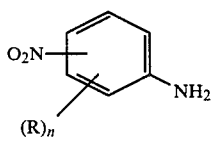
(VII)

wherein R and n are as stated above, is reacted with an isothiocyanate of the formula (VIII)

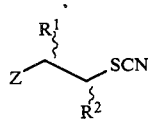
(VIII)

wherein $R^1$ and $R^2$ are as stated above, Z is a leaving group; or (a₅) a compound of the formula (IX)

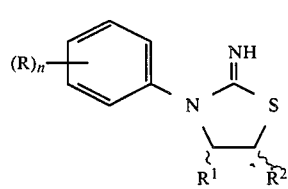
(IX)

wherein $R^1$, $R^2$, R and n are as stated above, is nitrated; or (a₆) a disulfide of the formula (XI)

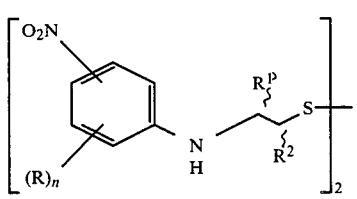
(XI)

wherein $R^1$, $R^2$, R and n are as stated above, is reacted with cyanogen bromide; or (b) for preparing compounds of the formula (I), wherein $R^3$ is amino, i.e. compounds of the formula (Ib)

(b₁) a compound of the formula (Ia), wherein $R^1$, $R^2$, R and n are as stated above, is reduced; or B₂) an isothiocyanate of the formula (II), wherein $R^1$, $R^2$, R and n are as stated above, is reduced, and the reaction product obtained is cyclized in the presence of an acid; or (b₃) an isothiuronium salt of the formula (VI), wherein $R^1$, $R^2$, R and n are as stated above, Z is a leaving ion, is reduced and the reaction product obtained is cyclized; or (b₄) the amino group of a compound of the formula (VII), wherein R and n are as stated above, is protected, the obtained compound of the formula (X)

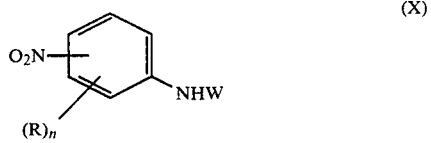
(X)

wherein R and n are as stated above, W is a protecting group, is reduced, the reaction product obtained is reacted with an isothiocyanate of the formula (VIII), wherein $R^1$ and $R^2$ are as stated above, Z is a leaving group, and finally the protecting group W is removed;

and, if desired, an obtained compound of the formula (I) is converted to a pharmaceutically acceptable acid addition salt.

In accordance with method a₁ of the invention, an isothiocyanate of the formula (II) is cyclized in the presence of an acid. Preferably, the cyclization is performed in a protic dipolar solvent, such as methanol or ethanol, at an elevated temperature, preferably at 60° to 100° C., for example at the boiling point of the reaction mixture. The acid used is preferably hydrogen chloride, also in the gaseous state. Other acids can also be employed. The product formed can be isolated from the mixture by conventional methods, e.g. cooling the mixture, evaporating the solvent or adding a solvent such as ether. Suitably, the product is isolated in the form of a crystalline salt.

According to method $a_2$ of the invention, a compound of the formula (III) is reacted with a compound of the formula (IVa) or a tautomeric form thereof represented by the formula (IVb). The reaction is suitably performed in an aprotic dipolar solvent such as dimethyl sulfoxide, dimethyl formamide, hexamethyl phosphoric triamide. In general, the reaction temperature does not exceed 100° C. The reaction mixture is heated until no starting compound of the formula (III) is present, then the reaction product is isolated by conventional method. For example, the reaction mixture is diluted with water and the product is extracted with a solvent immiscible with water, such as dichloromethane. Then, the solvent is removed and the product is separated in the form of the free base or as a crystalline acid addition salt, e.g. hydrochloride, hydrobromide, etc.

According to method $a_3$ of the invention, a compound of the formula (V) is reacted with thiourea in a protic dipolar solvent, preferably methanol or ethanol, at an elevated temperature, suitably at a temperature of 60° to 100° C., preferably at the boiling point of the reaction mixture. The reaction proceeds in several hours. When the starting compound of the formula (V) is no longer present, the solvent is removed, and the residue consisting of the compound of the formula (VI) is cyclized. It is preferred to perform the cyclization reaction by heating the compound of the formula (VI) with an acid, suitably acetic acid. Preferred starting substances are compounds of the formula (V), wherein Z represents a halo, such as chloro or bromo atom, or a lower alkylsulfonyloxy, e.g. mesyloxy, or an arylsulfonyloxy, e.g. p-toluenesulfonyloxy group.

In accordance with a method $a_4$ of the invention, the compounds of the formulae (VII) and (VIII) are reacted in an organic solvent having preferably a high boiling point, such as butanol, or in melt, without any solvent. The reaction temperature is, in general, about 100° to 150° C. It is preferred to perform the reaction at the reflux temperature. The product formed can be separated in the form of crystalline acid addition salts. Preferred starting substances are compounds of the formula (VIII), wherein Z stands for halo, e.g. chloro or bromo.

According to method $a_5$ of the invention, the nitration is performed suitably with nitric acid. The starting compound of the formula (IX) is dissolved in a suitable solvent, for example halogenated hydrocarbon, such as chloroform, and reacted with nitric acid at a temperature of 0° to 20° C. The nitro derivative obtained is isolated in a conventional manner: the excess of the nitric acid is removed suitably by treatment with cold water, the solvent is evaporated and the residual product is crystallized from a solvent.

According to method $a_6$ of the invention, a disulfide of the formula (XI) is reacted with cyanogen bromide in an inert organic solvent, preferably an ether, such as diethyl ether, tetrahydrofuran, dioxane, etc., with heating, suitably at the boiling point of the solvent. Preferably, the cyanogen bromide is employed in excess.

According to method $b_1$ of the invention, a compound of the formula (Ia) is reduced, suitably by catalytic hydrogenation. The hydrogenation is performed in a suitable solvent, for example lower alkanol such as methanol or ethanol, in the presence of a noble metal catalyst, preferably palladium. Catalysts applied to a carrier can be used. The hydrogenation reaction proceeds preferably at a pressure of 1 to 5 atm and at an elevated temperature or at room temperature. It is preferred to hydrogenate the compound of the formula (Ia) at room temperature and at atmospheric pressure. The product is separated in a conventional manner. Suitably, the catalyst is removed by filtration, the filtrate is evaporated or an excess of acid is added to obtain an acid addition salt of the product at a low temperature, e.g. about 0° C. Thus, the product is isolated in the form of either the free base or a crystalline acid addition salt.

In accordance with method $b_2$ of the invention, the starting compound of the formula (II) is reduced, preferably by catalytic hydrogenation. Preferred catalysts are noble metal catalysts, such as palladium, suitably applied to a carrier, e.g. charcoal. In general, the hydrogenation is performed in a suitable organic solvent, preferably a lower alkanol, such as methanol or ethanol, at a pressure of 1 to 5 atm and at room temperature or somewhat elevated temperatures. It is preferred to hydrogenate at room temperature and at atmospheric pressure. At the end of the reaction, the catalyst is removed by filtration, and the filtrate is treated with an excess of an acid, preferably hydrochloric acid or ethanesulfonic acid. The cyclization is carried out at lower temperatures, suitably at about 0° C. In general, the reaction time amounts to several hours. The product formed can be separated in the form of a crystalline acid addition salt. It is also possible to perform the hydrogenation of the compound of the formula (II) and the cyclization of the reduction product in a single step.

According to method $b_3$ of the invention, an isothiuronium salt of the formula (VI) is reduced, preferably by catalytic hydrogenation in the presence of a catalyst, such as a noble metal catalyst, preferably palladium which can be applied to a carrier, e.g. charcoal. The hydrogenation can be performed in a suitable solvent, for example lower alkanol, such as methanol or ethanol, or water, at a pressure of 1 to 5 atm and at room temperature or under heating. It is preferred to hydrogenate at room temperature and at atmospheric pressure. At the end of the reduction, the catalyst is removed by filtration, and the filtrate is heated at the boiling point of the solvent. The reduction and cyclization can be performed in a single step, too.

According to method $b_4$ of the invention, the amino group of the nitro compound of the formula (VII) is protected by means of a suitable protecting group, e.g. a lower alkoxycarbonyl, preferably tert.-butoxycarbonyl group. For example, the tert.-butoxycarbonyl group is introduced by reacting the compound of the formula (VII) with tert.-butylazido formiate in a neutral solvent, such as dioxane or tetrahydrofuran, in the presence of a base, such as triethyl amine, at room temperature. Then, the nitro group of the compound of the formula (X) is reduced, preferably by catalytic hydrogenation in the presence of a noble metal catalyst, e.g. palladium which can be applied to a carrier, such as charcoal. The hydrogenation is suitably performed at a pressure of about 1 to 5 atm and at room temperature or somewhat elevated temperatures. It is preferred to hydrogenate at room temperature and atmospheric pressure. At the end of the reduction the catalyst is removed by filtration, the filtrate is evaporated, and the residual product is reacted with a compound of the formula (VIII). The latter reaction can be carried out at higher temperatures, for example about 100° to 150° C., in a solvent or without any solvent. Suitable solvents for this purpose are organic solvents having high boiling point, such as butanol. The reaction proceeds in several hours. Then, the protecting group W is removed by conventional methods. For example, the alkoxycarbonyl protecting group is split off by treatment with aqueous hydrochloric acid, a solution of hydrogen chloride in an alcohol or with trifluoroacetic acid at room temperature or under heating. The above reaction sequence can also be performed in a single step.

The obtained compounds of the formula (I) can be reacted with inorganic or organic acids to give the corresponding acid addition salts. Similarly, the free base can be liberated from the acid addition salt by reacting the former with a base. These reactions can be carried out by conventional methods. For example, a compound of the formula (I) is reacted in a suitable inert solvent with a stoichiometric amount or a slight excess of an acid to obtain the acid addition salt thereof.

The starting compounds employed in the process of the invention are known or can be prepared in a manner known per se. The preparation of the starting substances is shown in the Examples in detail.

The starting compounds of the formula (XI) can be prepared by either reacting a compound of the formula (XIII)

wherein $R^1$ and $R^2$ are as stated above, with a nitro derivative of the formula (XII)

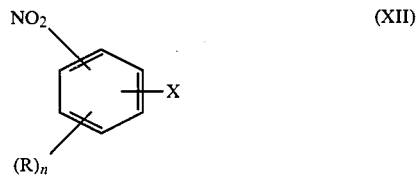

wherein R and n are as stated above, X represents halo, preferably chloro, or treating a compound of the formula (II) with an alkali metal alkoxide.

The novel compounds of the formula (I) possess valuable antidepressant, antiparkinsonic, antiepileptic and spasmolytic properties accompanied by a moderate analgesic activity. The activity of the compounds of the invention are examined by the following tests.

Test Methods (1) Acute toxicity on mice

The acute toxicity is determined on mice of both sex (CFLP breed, body weight 18 to 22 g). For each dosis 6 animals are employed. The compounds tested are administered orally in a volume of 20 ml/kg body weight. After the administration the animals are observed for 7 days. During this period the animals are fed with standard mouse feed and water ad libitum. The toxicity values are determined according to Litchfield-Wilcoxon's method.

(2) Tetrabenazine ptosis antagonism on mice

The tetrabenazine ptosis antagonism of the compounds are tested on groups consisting of 10 mice each. The animals are treated, orally, with different doses of the compounds tested, while the corresponding vehicle without the active agent is administered to the animals of the control group. 30 minutes after the introduction of the active agent or the vehicle, 50 mg/kg of tetrabenazine (3-isobutyl-9,10-dimethyl-1,2,3,4,6,7-hexahydrobenzo[a]quinolizine-2-one) are administered, intraperitoneally, and the animals with ptosis are counted 30, 60, 90 and 120 minutes after the administration of the tetrabenazine.

Evaluation: the average ptosis value is calculated in each group, and the deviation from the average obtained for the control group (inhibition) is given in percentage. From the data obtained $ED_{50}$ values are calculated.

(3) Reserpine ptosis antagonism on mice

Each group consisting of 10 mice are treated with 6 mg/kg of reserpine, subcutaneously. After 60 minutes, the compounds tested are administered to the animals, while the animals of the control group are treated with the corresponding vehicle without the active agent. The animals with ptosis are counted 60 and 120 minutes after the administration of the compounds to be tested. Evaluation is carried out as given under point (2) above.

(4) Yohimbine toxicity test on mice.

The examination is performed according to Quinton's method. Each group of animals consisting of 10 mice are treated with the compounds to be tested and the vehicle without active agent, respectively. After one hour a sublethal dosage of yohimbine in a volume of 20 ml/kg body weight is administered to the test groups, intraperitoneally. The number of the dead animals is recorded 1 and 24 hours after the administration of yohimbine.

(5) Inhibition of nicotine spasm

The test is carried out on mice according to Stone. One hour after the oral treatment a dosage of 1.4 mg/kg of nicotine is injected intravenously, and the spasm developed as well as the lethality are recorded at both the test and control groups.

(6) Inhibition of pentatetrazole spasm

The test is performed on mice according to a modified method of Banziger and Hane. Each group of animals consisting of 6 mice are treated, orally, with the compound to be tested and the vehicle without active agent, respectively. 1 hour after the treatment a dosage of 125 mg/kg of pentatetrazole is administered to each animal, intraperitoneally, and the tonic spasm of the lower limb extensor is recorded.

(7) Maximum inhibition of electroshock

The examination is carried out on mice weighing 20 to 25 g according to Swinyard. Electroshocks having the parameters of 50 Hz, 45 mA and 0.4 sec are employed by means of corneal electrodes. The complete inhibition of the tonic spasm of the lower limb extensor is taken as the criterium of the anticonvulsive action. One hour before the electroshock the animals are treated, orally, with the compounds to be tested and the vehicle without active agent, respectively.

(8) Antiperistaltic effect on mice

The antiperistaltic effect of the compounds is examined on mice weighing 20 to 25 g according to the method of Stickney and co-workers. Each dosis of the compound to be tested is administered, orally, 60 minutes prior to the administration of a 10 percent carbon suspension. The animals of the control group are treated, simultaneously and in a similar manner, with saline or other vehicle. 20 minutes after the administration of the carbon suspension, the animals are sacrificed, and the length of the entire small intestine as well as that of the small intestine filled with carbon are determined. The inhibition in relation to the control is calculated in percentage. The antiperistaltic effect is considered to be positive if the intestine portion filled with the carbon suspension does not exceed 50 percent of the total length of the small intestine. From the values thus-transformed $ED_{50}$ values are calculated.

(9) Analgesic effect on mice (writhing test)

The test is carried out on mice according to the modified method of Newbould. 0.75 percent acetic acid is administered to the animals in a volume of 20 ml/kg, intraperitoneally, and the characteristic "writhing reactions" are counted for a period of 5 minutes, starting from the fifth minute after challenge. The number of writhings is observed for both the treated and the control animals. The inhibition relative to the control group is evaluated in percentage.

The following compounds of the formula (I) were tested:

1 = 3-(2-amino-4-chlorophenyl)-2-iminothiazolidine dihydrochloride
2 = 3-(2-amino-5-chlorophenyl)-2-iminothiazolidine dihydrochloride
3 = 3-(2-amino-4-chlorophenyl)-2-imino-4-methyl-thiazolidine dihydrochloride
4 = 3-(2-amino-4-trifluoromethylphenyl)-2-imino-thiazolidine hydrochloride
5 = 3-(4-chloro-2-nitrophenyl)-2-iminothiazolidine hydrochloride
6 = 3-(2-nitro-4-trifluoromethylphenyl)-2-iminothiazolidine hydrochloride
7 = 3-(2-amino-4-methoxyphenyl)-2-iminothiazolidine dihydrochloride
8 = 3-(2-amino-4-chlorophenyl)-2-iminothiazolidine di(ethanesulfonate)
9 = 3-(5-chloro-2-nitrophenyl)-2-iminothiazolidine
10 = 3-(2-nitrophenyl)-2-iminothiazolidine
11 = 3-(4-methoxy-2-nitrophenyl)-2-iminothiazolidine hydrobromide
12 = 3-(2-amino-4-chlorophenyl)-2-imino-5-methyl-thiazolidine ethanesulfonate
13 = 3-(2-amino-4-methylphenyl)-2-iminothiazolidine
14 = 3-(4-aminophenyl)-2-imino-1,3-thiazolidine
15 = 3-(4-amino-2-nitrophenyl)-2-iminothiazolidine The results obtained are summarized in Tables I to IX.

TABLE I

| Compound No. | $LD_{50}$ in mg/kg | Tetrabenazine ptosis antagonism | |
|---|---|---|---|
| | | $ED_{50}$ in mg/kg | Therapeutical index |
| 1 | 700 | 18 | 39 |
| 2 | 800 | 25 | 32 |
| 4 | 1300 | 40 | 32.5 |
| 3 | 200 | 3 | 67 |
| 7 | 1200 | 16 | 75 |
| 8 | 1000 | 1.5 | 667 |
| 11 | 650 | 40 | 16.3 |
| 12 | 600 | 7.2 | 83 |
| Amitriptylin | 225 | 12 | 18.7 |

TABLE II

| Compound No. | $LD_{50}$ in mg/kg | Reserpine ptosis antagonism | |
|---|---|---|---|
| | | $ED_{50}$ in mg/kg | Therapeutical index |
| 1 | 700 | 50 | 14 |
| 3 | 200 | 3 | 67 |
| 4 | 1300 | 34 | 38 |
| 8 | 1000 | 20 | 50 |
| 11 | 650 | 40 | 16.3 |
| 13 | 1300 | 70 | 18.5 |
| Amitriptylin | 225 | 65 | 3.5 |

TABLE III

| Compound No. | $LD_{50}$ in mg/kg | Potentiation of yohimbine toxicity | |
|---|---|---|---|
| | | $ED_{50}$ in mg/kg | Therapeutical index |
| 2 | 800 | 50 | 16 |
| 8 | 1000 | 22 | 45.5 |
| 12 | 60 | 45 | 13.3 |
| 13 | 1300 | 52 | 25 |
| 14 | 400 | 20 | 20.0 |
| Amitriptylin | 225 | 12.5 | 18 |

TABLE IV

| Compound No. | $LD_{50}$ in mg/kg | Inhibition of nicotine lethality | |
|---|---|---|---|
| | | $ED_{50}$ in mg/kg | Therapeutical index |
| 1 | 700 | 25 | 5.6 |
| 3 | 200 | 6.4 | 31.3 |
| 5 | 1100 | 9 | 122 |
| 8 | 1000 | 12 | 83.3 |
| 10 | 700 | 50 | 24 |
| 11 | 650 | 45 | 14.4 |
| 12 | 600 | 6.0 | 100 |
| 13 | 1300 | 10 | 130 |
| Trihexyphenidyl | 365 | 40 | 9.1 |

TABLE V

| Compound No. | $LD_{50}$ in mg/kg | Inhibition of pentatetrazole spasm | |
|---|---|---|---|
| | | $ED_{50}$ in mg/kg | Therapeutical index |
| 1 | 700 | 22 | 31.8 |
| 2 | 800 | 78 | 10.2 |
| 3 | 200 | 7.8 | 25.6 |
| 4 | 1300 | 160 | 8.1 |
| 5 | 1100 | 66 | 16.6 |
| 8 | 1000 | 14 | 71.4 |
| 11 | 650 | 34 | 19.11 |
| 12 | 600 | 15 | 40 |
| Trimethadion | 2050 | 490 | 4.3 |

TABLE VI

| Compound No. | $LD_{50}$ in mg/kg | Inhibition of maximum electroshock | |
|---|---|---|---|
| | | $ED_{50}$ in mg/kg | Therapeutical index |
| 1 | 700 | 70 | 10 |
| 3 | 200 | 14 | 14.2 |
| 8 | 1000 | 80 | 12.5 |
| 12 | 600 | 12 | 30 |
| Trimethadion | 2050 | 400 | 5.3 |

TABLE VII

| Compound No. | $LD_{50}$ in mg/kg | Inhibition of intestinal peristalsis | |
|---|---|---|---|
| | | $ED_{50}$ in mg/kg | Therapeutical index |
| 4 | 1300 | 66 | 19.7 |
| 4 (diethane-sulfonate) | 1300 | 25 | 52 |
| 6 | 800 | 8 | 100 |
| 7 (diethane sulfonate) | 2000 | 200 | 10 |

TABLE VII-continued

| Compound No. | LD$_{50}$ in mg/kg | Inhibition of intestinal peristalsis | |
|---|---|---|---|
| | | ED$_{50}$ in mg/kg | Therapeutical index |
| 8 | 1000 | 95 | 10.5 |
| 9 | 700 | 18 | 38.9 |
| 10 | 700 | 140 | 5 |
| 11 | 650 | 105 | 6.2 |
| 14 | 400 | 50 | 4.4 |
| 15 | 1200 | 130 | 12 |
| Papaverine | 380 | 185 | 2.01 |

TABLE VIII

| Compound No. | LD$_{50}$ in mg/kg | Analgesic effect (writhing test) | |
|---|---|---|---|
| | | ED$_{50}$ in mg/kg | Therapeutical index |
| 2 | 800 | 43 | 18.6 |
| 4 (diethane-sulfonate) | 130 1300 | 160 | 8.1 |
| 8 | 1000 | 170 | 5.9 |
| 9 | 700 | 54 | 13 |
| 10 | 700 | 40 | 17.5 |
| 12 | 600 | 34 | 17.7 |
| 13 | 1300 | 160 | 8.1 |
| 15 | 1200 | 115 | 10.4 |
| Paracetamol | 510 | 180 | 2.9 |

TABLE IX

| Compound No. | LD$_{50}$ in mg/kg | Potentiation of narcosis | |
|---|---|---|---|
| | | ED$_{50}$ in mg/kg | Therapeutical index |
| 12 | 600 | 41.0 | 14.0 |
| Meprobamate | 1100 | 260.0 | 4.2 |

The invention also relates to pharmaceutical compositions containing as active agent at least one compound of the formula (I) or a pharmaceutically acceptable acid addition salt thereof, furthermore conventional solid or liquid pharmaceutical carrier(s). These compositions can be prepared by methods generally known in the pharmaceutical industry.

The pharmaceutical compositions are presented preferably in the form of orally administerable preparations, such as tablets, capsules, coated tablets, solutions, suspensions, etc., or parenterally administerable compositions, such as sterile solutions or suspensions.

The orally administerable pharmaceutical compositions contain conventional carriers, such as gelatin, sorbitol, lactose, sugar, starch, calcium phosphate, polyvinylpyrrolidone, magnesium stearate, talc, polyethylene glycol, silica, sodium lauryl sulfate, etc.

The compositions for parenteral administration contain the usual carriers of such type of compositions, for example sorbitol, sugar solution, carboxymethylcellulose, glycerol, propylene glycol, ethanol, etc.

The daily dose of the compound of the invention is, in general, 0.1 to 1000 mg/kg, preferably 1 to 100 mg/kg.

The invention is further elucidated by means of the following non-limiting examples.

EXAMPLE 1

Preparation of N-(2-bromoethyl)-4-methoxy-2 nitroaniline 100 g (0.23 moles) of N-(2-bromoethyl)-N-tosyl-4-methoxy-2-nitroaniline [Lempert, K. et al., Tetrahedron, 39, 1212 (1983)] are added to 100 ml of concentrated sulfuric acid under stirring and cooling with ice. The solution is left to stand for 24 hours, then poured onto 300 g of ice, filtered and washed with water thoroughly.

62 g (97%) of the title compound are obtained in the form of red crystal powder. M.p.: 53°–55° C. (methanol).

Analysis for $C_9H_{11}BrN_2O_3$ (Mw.: 275.1). Calculated: Br 29.05%, N 10.18%. Found: Br 29.19%, N 10.21%.

EXAMPLE 2

Preparation of 4-chloro-N-(2-methyl-2-mesyloxyethyl)-2-nitroaniline

To a solution of 16 g (0.07 moles) of 4-chloro-N-(2-hydroxy-2-methyl-ethyl)-2-nitroaniline in 50 ml of anhydrous pyridine 11.4 g (17 ml, 0.1 mole) of mesyl chloride are added at 0° C. drop by drop. The mixture is stirred for another 3 hours, then poured into 200 ml of ice water, filtered and washed with water.

14 g (65%) of the title compound are obtained in the form of orange red crystal powder. M.p.: 106°–108° C. (methanol).

Analysis for $C_{10}H_{13}ClN_2O_3S$ (Mw.: 308.8). Calculated: Cl 11.49%, N 9.07%, S 10.40%. Found: Cl 11.52%, N 9.25%, D 10.52%.

EXAMPLE 3

Preparation of N-(2-mesyloxyethyl)-4-chloro-2-nitroaniline

To a solution of 21.7 g (0.1 mole) of 2-(4-chloro-2-nitroanilino)-ethanol in 60 ml of pyridine 16.3 g (10.8 ml, 0.14 moles) of methanesulfonyl chloride are added, drop by drop. The addition of the methanesulfonyl chloride is performed at a temperature not exceeding 5° C. under ice cooling. The mixture is stirred for an hour under cooling, then it is poured into 400 ml of ice water. The yellow crystals separated are filtered, washed thoroughly with ice-cold water, dried and recrystallized from 500 ml of methanol.

22 g (75%) of the title compound are obtained in the form of yellow crystalline powder. M.p.: 108°–109° C. (methanol).

Analysis for $C_9H_{11}ClN_2O_5S$ (Mw.: 294.8). Calculated: C. 12.04%, N 9.50%, S 10.88%. Found: Cl 12.34%, N 9.30%, S 10.52%.

TLC (benzene-acetone 4:1) $R_f=0.8$.

EXAMPLE 4

Preparation of 4-methyl-N-(2-mesyloxyethyl)-2-nitroaniline

To a solution of 7.5 g (0.038 moles) of 2-(4-methyl-2-nitroanilino)-ethanol [Matsukawa, T. and Shirakawa, K., J. Pharm. Soc. Japan, 63, 370 (1943); C.A., 45, 2876 (1951)] in 23 ml of pyridine 4.2 ml (0.054 moles) of methanesulfonyl chloride are added drop by drop, under ice cooling, at a temperature not exceeding 5° C. The reaction mixture is stirred for another 4 hours at the above temperature, then poured into 120 ml of ice water. The crystals separated are filtered, washed with some cold water and dried.

9.7 g (93%) of the title compound are obtained in the form of yellow crystalline powder. M.p.: 65°–67° C. (dichloromethane-ether).

Analysis for $C_{10}H_{14}N_2O_5S$ (Mw.: 274.3). Calculated: C 43.79%, H 5.14%, N 10.21%, S 11.69%. Found: C 43.78%, H 5.20%, N 9.88%, S 11.62%.

EXAMPLE 5

Preparation of 5-chloro-N-(2-mesyloxyethyl)-2-nitroaniline

To a solution of 21.7 g (0.1 mole) of 2-(5-chloro-2-nitroanilino)-ethanol in 60 ml of pyridine, 16.3 g (10.8 ml, 0.14 mole) of methanesulfonyl chloride are added, drop by drop, under ice cooling, at a temperature not exceeding 5° C. The reaction mixture is stirred for an hour under cooling, then poured into 500 ml of ice water. The crystals separated are filtered, washed thoroughly, with ice-cold water and dried.

Thus, 29 g (98%) of the title compound are obtained in the form of lemon-colored crystalline powder. M.p.: 101°–102° C. (methanol).

Analysis for $C_9H_{11}ClN_2O_5S$ (Mw.: 294.8). Calculated: Cl 12.04%, N 9.50%, S 10.88%. Found: Cl 11.71%, N 9.45%, D 11.00%.

EXAMPLE 6

Preparation of N-(2-mesyloxyethyl)-4-trifluoromethyl-2-nitroaniline

To a solution of 20 g (0.077 moles) of 2-(4-trifluoromethyl-2-nitroanilino)-ethanol in 100 ml of pyridine 17.6 g (12 ml, 0.16 moles) of methanesulfonyl chloride are added, drop by drop, at 0° C. The reaction mixture is stirred for 40 minutes, then poured into 1 liter of ice water. The crystals separated are filtered, washed thoroughly with water and dried.

19 g (75%) of the title compound are obtained in the form of lemon-colored crystal powder. M.p.: 68°–70° C. (ethyl acetate-petrolether).

Analysis for $C_{10}H_{11}F_3N_2O_5S$ (Mw.: 328.3). Calculated: N 8.53%, S 9.76%. Found: N 8.56%, S 10.21%.

TLC (benzene-acetone 4:1) $R_f = 0.65$.

EXAMPLE 7

Preparation of 2-nitro-N-(2-mesyloxyethyl)-aniline

To a solution of 2.5 g (0.013 moles) of 2-nitro-N-(2-hydroxyethyl)-aniline in 25 ml of anhydrous pyridine 2.3 g (1.6 ml, 0.02 moles) of methanesulfonyl chloride are added drop by drop at 0° C. The reaction mixture is stirred for an hour, then poured into 200 ml of ice water. The crystals are filtered, washed thoroughly with water and dried.

3.1 g (91%) of the title compound are obtained in the form of yellowish red crystals. M.p.: 86°–87° C. (ethanol).

Analysis for $C_9H_{12}N_2O_3S$ (Mw.: 260.3). Calculated: C 41.53%, H 4.65%, N 10.76%, S 12.32%. Found: C 41.76%, H 4.41%, N 10.63%, S 12.54%.

EXAMPLE 8

Preparation of methyl 4-(N-2-mesyloxyethylamino)-3-nitrobenzoate

To a solution of 24 g (0.1 mole) of methyl 4-(N-2-hydroxyethylamino)-benzoate in 100 ml of pyridine 17.6 g (12.4 ml, 0.15 moles) of methanesulfonyl chloride are added, drop by drop, at 0° C. The reaction mixture is stirred for an hour, then poured into 250 ml of ice water. The crystals are filtered, washed thoroughly with water and dried.

20.6 g (65%) of the title compound are obtained in the form of red-brown crystals. M.p.: 109°–111° C. (methanol).

Analysis for $C_{11}H_{14}N_2O_7S$ (Mw.: 318.3). Calculated: C 41.50%, H 4.43%, N 8.80%, S 10.07%. Found: C 41.80%, H 4.61%, N 8.91%, S 10.24%.

EXAMPLE 9

Preparation of 2-nitro-4-trifluoromethyl-N-(2-thiocyanatoethyl)-aniline 10.4 g (0.03 moles) of 4-trifluoromethyl-N-(2-mesyloxyethyl)-2-nitroaniline are boiled with 6 g (0.06 moles) of potassium rhodanide in 200 ml of ethanol for 6 hours, under stirring. The reaction mixture is poured into 500 ml of water, the crystals are filtered, washed with water and dried.

7.4 g (85%) of the title compound are obtained in the form of yellow needles. M.p.: 115°–117° C. (methanol).

Analysis for $C_{10}H_8N_3O_2S$ (Mw.: 291.3). Calculated: N 14.42%, S 11.01%. Found: N 14.38%, S 11.46%.

EXAMPLE 10

Preparation of 4-methoxy-2-nitro-N-(2-thiocyanatoethyl)-aniline 5.5 g (0.02 moles) of 4-methoxy-2-nitro-N-(2-bromoethyl)-aniline are boiled with 3 g (0.03 moles) of potassium rhodanide in 50 ml of ethanol for 8 hours under stirring. The reaction mixture is poured into 200 ml of water, the crystals are filtered, washed with water and dried.

4.5 g (89%) of the title compound are obtained in the form of orange red crystals. M.p.: 116°–118° C. (ethanol).

Analysis for $C_{10}H_{11}N_3O_3S$ (Mw.: 253.3). Calculated: C 47.41%, H 4.38%, N 16.60%, S 12.67%. Found: C 47.51%, H 4.10%, N 16.75%, S 12.62%.

EXAMPLE 11

Preparation of 5-chloro-2-nitro-N-(2-thiocyanatoethyl)-aniline 10 g (0.034 moles) of N-(2-mesyloxyethyl)-5-chloro-2-nitroaniline and 6.6 g (0.068 moles) of potassium rhodanide are boiled in 200 ml of ethanol for 5 hours under stirring. The inorganic salts separated are filtered, and about 200 ml of water are added to the warm filtrate. On cooling the crystals separated are filtered, and washed thoroughly with water.

8.1 g (92%) of the title compound are obtained in the form of yellow crystal powder. M.p.: 115°–116° C.

Analysis for $C_9H_8ClN_3O_2S$ (Mw.: 257.7). Calculated: Cl 13.77%, N 16.30%, S 12.44%. Found: Cl 14.09%, N 16.32%, S 19.79%.

TLC (cyclohexane-ethyl acetate 2:3) $R_f = 0.6$.

EXAMPLE 12

Preparation of 4-chloro-2-nitro-N-(2-thiocyanatoethyl)-aniline 5.9 g (0.02 moles) of N-(2-mesyloxyethyl)-4-chloro-2-nitroaniline and 4 g (0.041 moles) of potassium rhodanide are refluxed in 200 ml of ethanol for 5 hours under stirring. The inorganic salts are separated from the hot solution by filtration, and about 100 ml of water are added to the warm filtrate. On cooling, the crystals are filtered, washed thoroughly with water and dried.

5.0 g (97%) of the title compound are obtained in the form of orange-colored crystal powder. M.p.: 154°–155° C. (isopropanol).

Analysis for $C_9H_8N_3ClO_2S$ (M.w.: 257.7). Calculated: C 41.94%, H 3.12%, Cl 13.77%, N 16.30%. Found: C 42.13%, H 3.07%, Cl 13.94%, N 16.59%.

TLC (cyclohexane-ethyl acetate 2:3) $R_f=0.7$.

EXAMPLE 13

Preparation of 4-chloro-2-nitro-N-(2-methyl-2-thiocyanatoethyl)-aniline 13 g (0.042 moles) of 4-chloro-N-(2-methyl-2-mesyloxyethyl)-2-nitroaniline and 5.8 g (0.06 moles) of potassium rhodanide are refluxed in 60 ml of ethanol for 4 hours. The inorganic salts are separated from the hot solution by filtration, then the filtrate is evaporated under reduced pressure. The residual oil is treated with water to induce crystallization, the crystals are filtered, washed thoroughly with water, and dried.

8.2 g (72%) of the title compound are obtained in the form of yellowish red crystals. M.p.: 69°-70° C. (methanol).

Analysis for $C_{10}H_{10}ClN_3O_2S$ (Mw.: 271.8). Calculated: Cl 13.06%, N 15.46%, S 11.80%. Found: Cl 12.96%, N 15.61%, S 11.73%.

EXAMPLE 14

Preparation of 2-nitro-N-(2-thiocyanatoethyl)-aniline 2.6 g (0.01 mole) of 2-nitro-N-(2-mesyloxyethyl)-aniline and 1.95 g (0.02 moles) of potassium rhodanide are refluxed in 40 ml of isopropanol for 3 hours. The solvent is evaporated under reduced pressure, the residue is treated with 20 ml of dichloromethane, filtered, the filtrate is evaporated, and the residue crystallized from ethanol.

1.9 g (85%) of the title compound are obtained in the form of yellowish red crystals. M.p.: 112°-113° C. (ethanol).

Analysis for $C_9H_9N_3O_2S$ (Mw.: 223.3). Calculated: C 48.42%, H 4.06%, N 18.82%, S 14.36%. Found: C 48.52%, H 4.13%, N 18.80%, S 14.56%.

EXAMPLE 15

Preparation of methyl 3-nitro-4-[N-(2-thiocyanatoethyl)-amino-7-benzoate 9.6 (0.03 moles) of methyl 4-[N-(2-mesyloxyethyl)-amino-]-3-nitrobenzoate are boiled with 5.8 g (0.06 moles) of potassium rhodanide in 100 ml of methanol for 18 hours. The reaction mixture is evaporated under reduced pressure, the residual crystals are treated with water, filtered and washed with water.

In this way 6.7 g (79%) of the title compound are obtained in the form of yellowish red crystals. M.p.: 102°-103° C. (methanol).

Analysis for $C_{11}H_{11}N_3O_4S$ (Mw.: 281.3). Calculated: C 46.97%, H 3.94%, N 14.94%, S 11.40%. Found: C 46.72%, H 4.24%, N 14.92%, S 11.36%.

EXAMPLE 16

Preparation of 4-methyl-2-nitro-N-(2-thiocyanatoethyl)-aniline

A mixture of 9.5 g (0.035 mole) of 4-methyl-N-(2-mesyloxyethyl)-2-nitroaniline, 6.4 g (0.066 moles) of potassium rhodanide and 70 ml of anhydrous dimethyl formamide is stirred at 140° C. for 1 hour. The cooled reaction mixture is admixed to 100 ml of water, cooled, the crystals separated are filtered, washed with some cold water and dried.

7.5 g (91%) of the title compound are obtained, m.p.: 123°-125° C. (dichloromethane-ether).

Analysis for $C_{10}H_{11}N_3O_2S$ (M.w.: 237.3). Calculated: C 50.62%, H 4.67%, N 17.71%, S 13.51%. Found: C 50.42%, H 4.67%, N 17.57%, S 13.33%.

EXAMPLE 17

Preparation of 2-imino-3-(2'-amino-4'-methoxyphenyl)-thiazolidine di(ethanesulfonate)

2.5 g (0.01 mole) of 4-methoxy-2-nitro-N-(2-thiocyanatoethyl)-aniline are hydrogenated in the mixture of 50 ml of methanol and 50 ml of dichloromethane in the presence of 0.3 g of palladium/carbon catalyst. Then, the mixture cooled to 0° C. is filtered, and 2.2 g (1.7 ml, 0.02 moles) of ethanesulfonic acid are added to the filtrate. The reaction mixture is stirred for 1 hour at 0° C., then evaporated at reduced pressure. The crystalline residue is treated with acetone, filtered, washed with acetone and dried.

3.1 g (70%) of the title compound are obtained in the form of colorless thread-like crystals. M.p.: 187° C. (ethanol).

Analysis for $C_{14}H_{25}N_3O_7S_3$ (Mw.: 443.6). Calculated: N 9.47%, S 21.69%. Found: N 9.49%, S 22.02%.

EXAMPLE 18

Preparation of 2-imino-3-(2'-amino-4'-chlorophenyl)-thiazolidine di(ethanesulfonate)

2.6 g (0.01 mole) of 4-chloro-2-nitro-N-(2-thiocyanatoethyl)-aniline are hydrogenated in 50 ml of methanol and 50 ml of dichloromethane in the presence of 0.3 g of palladium/carbon catalyst. The mixture cooled to 0° C. is filtered and 2.2 g (1.7 ml, 0.02 moles) of ethanesulfonic acid are added to the filtrate. The mixture obtained is stirred for 1 hour at the same temperature, then evaporated under reduced pressure. The residue is crystallized from a mixture of methanol and ether.

3.5 g (78%) of the title compound are obtained in the form of colorless, thread-like crystals. M.p.: 162°-164° C. (methanol-ether).

Analysis for $C_{13}H_{23}ClN_3O_6S_3$ (Mw.: 449.0). Calculated: Cl 7.90%, N 9.35%, S 21.42%. Found: Cl 8.22%, N 9.14%, S 21.20%.

TLC (methanol) $R_f=0.8$.

EXAMPLE 19

Preparation of 2-imino-3-(2'-amino-4'-methoxyphenyl)-thiazolidine dihydrochloride 2.5 g (0.01 mole) of 4-methoxy-2-nitro-N-(2-thiocyanatoethyl)-aniline is hydrogenated in a mixture of 50 ml of dichloromethane and 50 ml of methanol in the presence of 0.5 g of 5 percent palladium/carbon catalyst. The mixture is cooled to 0° C., the catalyst is removed by filtration, the filtrate is saturated with gaseous hydrogen chloride, then evaporated in vacuo. The oily residue is treated with ethanol, filtered, washed with ether and dried.

1.8 g (61%) of the title compound are obtained. M.p.: 198°-200° C. (decomp.) (ethanol-ether).

Analysis for $C_{10}H_{15}Cl_2N_3OS$ (Mw.: 296.2). Calculated: Cl 23.94%, N 14.18%, S 10.83%. Found: Cl 24.38%, N 14.10%, S 11.04%.

TLC (acetic acid) $R_f=0.6$.

EXAMPLE 20

Preparation of
2-imino-3-(2'-amino-4'-methoxycarbonylphenyl)-thiazolidine dihydrochloride 2.8 g (0.01 mole) of methyl 3-nitro-4-N-(2-thiocyanatoethyl)-aminobenzoate are hydrogenated in 150 ml of methanol in the presence of 1 g of 5 percent palladium/carbon catalyst. The mixture is cooled to 0° C., the catalyst is removed by filtration, the filtrate is saturated with gaseous hydrogen chloride, then evaporated under reduced pressure. The residue is treated with acetone, filtered, washed with acetone and dried.

In this way 2.4 g (74%) of the title compound are obtained in the form of colorless crystal powder. M.p.: 163°–164° C. (dec.) (methanol-ether).

Analysis for $C_{11}H_{15}Cl_2N_3O_2S$ (Mw.: 324.2). Calculated: Cl 21.87%, N 12.96%, S 9.89%. Found: Cl 21.91%, N 12.77%, S 10.24%.

EXAMPLE 21

Preparation of
2-imino-3-(2'-amino-4'-methylphenyl)-thiazolidine dihydrochloride 1.0 g (0.0042 moles) of 4-methyl-2-nitro-N-(2-thiocyanatoethyl)-aniline are hydrogenated in 50 ml of dichloromethane and 50 ml of methanol in the presence of 0.3 g of 5 percent palladium/carbon catalyst. The mixture is cooled to 0° C., the catalyst is removed by filtration, the filtrate is saturated with dry gaseous hydrogen chloride, then evaporated at room temperature in vacuo. The residue is treated with ethyl acetate, filtered, washed with some cold ethyl acetate and dried.

0.8 g (68%) of the title compound are obtained. M.p.: 178° C. (methanol-ethyl acetate).

Analysis for $C_{10}H_{15}Cl_2N_3S$ (Mw.: 280.2). Calculated: C 42.86%, H 5.40%, Cl 25.30%, N 15.00%, S 11.44%. Found: C 42.52%, H 5.77%, Cl 24.78%, N 14.90%, S 11.21%.

TLC (5 percent aqueous sodium chloride-ethanol 1:19) $R_f=0.65$.

EXAMPLE 22

Preparation of
2-imino-3-(2'-amino-4'-chlorophenyl)-thiazolidine dihydrochloride 4 g (0.016 moles) of 4-chloro-2-nitro-N-(2-thiocyanatoethyl)-aniline are hydrogenated in 100 ml of dioxane in the presence of 1 g of 5 percent palladium/carbon catalyst. The mixture is cooled to 0° C., the catalyst is removed by filtration, the filtrate is saturated with dry gaseous hydrogen chloride, then evaporated in vacuo using a water bath of 40° C. at the most. The residual oil is treated with some ethanol, filtered, washed with ethanol, then with ether and dried.

3.7 g (76%) of the title compound are obtained in the form of colorless crystal powder, M.p.: 185°–186° C. (dec.) (methanol-ether).

Analysis for $C_9H_{12}Cl_3N_3S$ (Mw.: 300.6). Calculated: Cl 35.38%, N 13.97%, S 10.66%. Found: Cl 35.26%, N 14.03%, S 11.02%.

EXAMPLE 23

Preparation of
2-imino-3-(2'-amino-5'-chlorophenyl)-thiazolidine dihydrochloride 4 g (0.016 moles) of 5-chloro-2-nitro-N-(2-thiocyanatoethyl)-aniline are hydrogenated in 80 ml of anhydrous dioxane in the presence of 1 g of 5 percent palladium/carbon catalyst at room temperature. At the end of the reduction the mixture is cooled to 0° C., the catalyst is removed by filtration, the filtrate is saturated with dry gaseous hydrogen chloride, then evaporated under reduced pressure using a water bath of 40° C. at the most. The residual oil is treated with some ethanol, the crystals are filtered, washed with some ethanol, then with ether and dried.

3.2 g (67%) of the title compound are obtained in the form of colorless crystal powder. M.p.: 184°–185° C. (dec.) (methanol-ether).

Analysis for $C_9H_{12}Cl_3N_3S$ (Mw.: 300.6). Calculated: Cl 35.38%, N 13.97%, D 10.66%. Found: Cl 35.31%, N 13.75%, S 10.82%.

TLC (benzene-methanol 1:1) R=0.4.

EXAMPLE 24

Preparation of
2-imino-3-(2'-amino-4'-trifluoromethylphenyl)-thiazolidine dihydrochloride 10.5 g (0.036 moles) of 2-nitro-4-trifluoromethyl-N-(2-thiocyanatoethyl)-aniline are hydrogenated in 100 ml anhydrous dioxane in the presence of 2 g of 5 percent palladium/carbon catalyst. The catalyst is removed by filtration, the filtrate is saturated with dry gaseous hydrogen chloride under cooling, then evaporated in vacuo. The residue is treated with anhydrous acetone, filtered, washed with acetone and dried.

10.5 g (87%) of the title compound are obtained, M.p.: 171°–172° C. (dec.) (methanol-ether).

Analysis for $C_{10}H_{12}Cl_2F_3N_3S$ (Mw.: 334.2). Calculated: Cl 21.22%, N 12.57%, S 9.59%. Found: Cl 20.78%, N 12.63%, S 9.40%.

EXAMPLE 25

Preparation of 2-imino-3-(2'-aminophenyl)-thiazolidine dihydrochloride 6.7 g (0.03 moles) of 2-nitro-N-(2-thiocyanatoethyl)-aniline are hydrogenated in 150 ml of anhydrous dioxane in the presence of 2 g of 5 percent palladium/carbon catalyst. The catalyst is removed by filtration, the filtrate is saturated with dry gaseous hydrogen chloride under cooling, then evaporated in vacuo. The residue is treated with anhydrous ethanol, filtered, washed with ether and dried.

6.5 g (81%) of the title compound are obtained in the form of colorless crystal powder. M.p.: 178°–179° C. (methanol-ether).

Analysis for $C_8H_{13}Cl_2N_3S$ (Mw.: 266.2). Calculated: Cl 26.63%, N 15.78%, S 12.04%. Found: Cl 26.50%, N 15.65%, S 12.44%.

TLC (benzene-methanol 2:1) $R_f=0.3$.

EXAMPLE 26

Preparation of 2-imino-3-(2'-amino-4'-chlorophenyl)-5-methylthiazolidine dihydrochloride 2.7 g (0.01 mole) of 4-chloro-2-nitro-N-(2-methyl-2-thioacyanathoethyl)-aniline are hydrogenated in 50 ml of methanol in the presence of 1 g of 5 percent palladium/carbon catalyst. The reaction mixture is cooled to 0° C., the catalyst is removed by filtration and the filtrate is saturated with gaseous hydrogen chloride. The solution is evaporated under reduced pressure, and the residue is treated with anhydrous acetone to induce crystallization.

In this way 2.1 g (67%) of the title compound are obtained in the form of colorless thread-like crystals. M.p.: 172°–174° C. (dec.) (methanol-acetone).

Analysis for $C_{10}H_{14}Cl_3N_3S$ (Mw.: 314.7). Calculated: C 38.17%, H 4.48%, N 13.35%, S 10.19%. Found: C 38.52%, H 4.19%, N 13.53%, S 9.71%.

EXAMPLE 27

Preparation of 2-imino-3-(4'-aminophenyl)-thiazolidine 1.1 g (0.005 moles) of 2-imino-3-(4'-nitrophenyl)-thiazolidine are hydrogenated in 30 ml of anhydrous dioxane in the presence of 0.8 g of 10 percent palladium/carbon catalyst. The catalyst is removed by filtration, the filtrate is evaporated in vacuo, the crystalline residue is treated with ether, filtered and dried.

Thus, 0.68 g (70%) of the title compound are obtained in the form of colorless crystals. M.p.: 148° C. (isopropanol-petroletherer).

Analysis for $C_9H_{11}N_3S$ (Mw.: 193.3). Calculated: C 55.93%, H 5.74%, N 21.74%. Found: C 56.13%, H 5.83%, N 21.62%.

TLC (ethanol-dioxane-conc. aqueous ammonia 3:6:1) $R_f=0.6$.

EXAMPLE 28

Preparation of 2-imino-3-(2'-nitrophenyl)-thiazolidine hydrochloride

Gaseous hydrogen chloride is led into a solution of 0.4 g (0.018 moles) of 2-nitro-N-(2-thiocyanatoethyl)-aniline in 50 ml of ethanol for 30 minutes, while the solution is boiled. On cooling the crystals separated are filtered, washed with ether and dried.

3.9 g (83%) of the title compound are obtained in the form of yellow crystal powder. M.p.: 286° C. (dec.) (ethanol-ether).

Analysis for $C_9H_{10}ClN_3O_2S$ (Mw.: 259.8). Calculated: Cl 13.66%, N 16.17%, S 12.34%. Found: Cl 13.54%, N 16.23%, S 12.04%.

Deliberation of the Base

A solution of 1.3 g (0.005 moles) of the hydrochloride prepared above in 30 ml of water is made alkaline to pH=9 with 40 percent aqueous sodium hydroxide. The crystals separated are filtered, washed with water and crystallized from a mixture of ethyl acetate and petrolether.

1.0 g (90%) of 2-imino-3-(2'-nitrophenyl)-thiazolidine are obtained in the form of yellow crystal powder. M.p.: 127° C.

EXAMPLE 29

Preparation of 2-imino-3-(2'-nitrophenyl)-thiazolidine hydrochloride

A mixture of 0.8 g (0.008 moles) of 2-aminothiazolidine, 0.56 g (0.004 moles) of o-fluoro-nitrobenzene and 10 ml of anhydrous dimethyl sulfoxide is stirred at 80° C. for 3 hours. The solution is poured into 50 ml of water and extracted 3 times with 20 ml of dichloromethane. The organic phases are combined, dried over magnesium sulfate, and evaporated in vacuo. The oily residue is crystallized from a mixture of ethyl acetate and petroleum ether.

0.4 g (46%) of the title compound are obtained in the form of yellow crystal powder. M.p.: 127° C. (ethyl acetate-petroleum ether).

On the basis of melting point, infrared spectra and thin-layer chromatography, the product thus-obtained is identical with the base prepared in Example 28.

TLC (toluene-ethyl acetate 1:1) $R_f=0.12$.

EXAMPLE 30

Preparation of 2-imino-3-(4'-methyl-2'-nitrophenyl)-thiazolidine hydrochloride 2.0 g (0.0084 moles) of 4-methyl-2-nitro-N-(2-thiocyanatoethyl)-aniline are boiled in 50 ml of ethanol for 1 hour, while gaseous hydrogen chloride is introduced into the solution. The heterogeneous reaction mixture becomes homogeneous at the end of the reaction. The solution is concentrated to about half of its volume, and the crystals separated on cooling are filtered, washed with some ethanol, then with ether and dried.

1.8 g (78%) of the title compound are obtained in the form of yellow crystal powder. M.p.: 287°–289° C.

Deliberation of the Base 1 g of the hydrochloride prepared above are stirred thoroughly in a mixture of 20 ml of saturated aqueous potassium carbonate solution and 25 ml of chloroform. The phases are separated, the aqueous phase is extracted twice with 10 ml of chloroform each time. The combined organic phases are dried over anhydrous magnesium sulfate, and evaporated.

In this way 0.78 g (90%) of 2-amino-3-(4'-methyl-2'-nitrophenyl)-thiazolidine are obtained in the form of pale yellow crystal powder. M.p.: 132°–134° C. (ether-petroleum ether).

Analysis for $C_{10}H_{11}N_3O_2S$ (Mw.: 237.3). Calculated: C 50.62%, H 4.67%, N 17.71%, S 13.51%. Found: C 50.52%, H 4.59%, N 17.89%, S 13.69%.

EXAMPLE 31

Preparation of 2-imino-3-(4'-methoxycarbonyl-2'-nitrophenyl)-thiazolidine

The solution of 1 g (0.01 mole) of 2-aminothiazolidine and 1 g (0.005 moles) of methyl 4-fluoro-3-nitrobenzoate [Finger, G. C. and Kruse, C. W., J. Am. Chem. Soc., 78, 6034 (1956)] in 10 ml of anhydrous dimethyl formamide are stirred at 90° C. for 1 hour, then poured into 60 ml of water and extracted 3 times with 20 ml of dichloromethane each time. The organic solution is dried over anhydrous magnesium sulfate and evaporated under reduced pressure. The residue is treated with some ethyl acetate, filtered, washed with ether and dried.

0.9 g (64%) of the title compound are obtained in the form of yellow crystal powder. M.p.: 156° C. (ethyl acetate-petroleum ether).

Analysis for $C_{11}H_{11}N_3O_4S$ (Mw.: 281.3). Calculated: C 46.97%, H 3.94%, N 14.34%, S 11.40%. Found: C 47.02%, H 4.16%, N 14.07%, S 11.30%.

TLC (toluene-ethyl acetate 1:1) $R_f=0.25$.

EXAMPLE 32

Preparation of
2-imino-3-(4'-methoxycarbonyl-2'-nitrophenyl)-thiazolidine hydrochloride Into a mixture of 0.5 g (0.0018 moles) of methyl 3-nitro-4-N-(2-thiocyanatoethyl)-aminobenzoate and 10 ml of anhydrous methanol, dry gaseous hydrogen chloride is introduced for 1 hour under reflux. The solution obtained is concentrated to about a third of its volume, and ether is added to induce crystallization. On cooling the crystals are removed by filtration, washed with ether and dried.

0.4 g (71%) of the title compound are obtained. M.p.: 242° C. (dec.) (methanol-ether).

Deliberation of the Base 1 g of the hydrochloride prepared above are stirred thoroughly in a mixture of 20 ml of saturated aqueous sodium carbonate solution and 30 ml of dichloromethane. The phases are separated, the aqueous phase is extracted twice with 10 ml of dichloromethane each time. The organic solutions are combined, dried and evaporated.

In this way, 0.8 g (80%) of 2-imino-3-(4'-methoxy-2'-nitrophenyl)-thiazolidine are obtained. M.p. 156° C.

On the basis of the melting point, infrared spectra and thin-layer chromatography, the product thus-obtained is identical with the base prepared in Example 31.

EXAMPLE 33

Preparation of
2-imino-3-(2'-nitro-4'-trifluoromethylphenyl)-thiazolidine

The solution of 1.04 g (0.005 moles) of 1-fluoro-2-nitro-4-trifluoromethylbenzene [Finger, G. C. and Kruse, C. W., J. Am. Chem. Soc., 78, 6034 (1965)] and 1 g (0.01 mole) of 2-aminothiazolidine in 10 ml of anhydrous dimethyl sulfoxide is heated at 90° C. for 1 hour, then poured into 60 ml of water. The mixture is extracted 3 times with 20 ml of dichloromethane each time, the combined organic solutions are dried over anhydrous magnesium sulfate, and evaporated under reduced pressure. The residue is treated with some ethyl acetate, filtered, washed with ether and dried.

0.5 g (35%) of the title compound are obtained. M.p.: 153° C.

TLC (toluene-ethyl acetate 1:1) $R_f=0.3$.

The base obtained can be converted to the hydrochloride by means of methanol saturated with hydrogen chloride. On the basis of melting point, infrared spectra and thin-layer chromatography the salt thus-obtained is identical with the hydrochloride prepared in Example 34.

EXAMPLE 34

Preparation of
2-imino-3-(2'-nitro-4'-trifluoromethylphenyl)-thiazolidine hydrochloride Into a solution of 5 g (0.017 mole) of 2-nitro-4-trifluoromethyl-N-(2-thiocyanatoethyl)-aniline in 30 ml of ethanol dry gaseous hydrogen chloride is introduced for 1 hour under reflux. At the end of the reaction crystals separate. On cooling the crystal mass is separated by filtration, washed with ether and dried.

Thus, 4.5 g (81%) of the title compound are obtained in the form of pale yellow crystal powder. M.p.: 295° C. (dec.) (ethanol).

Analysis for $C_{10}H_9ClF_3N_3O_2S$ (Mw.: 327.8). Calculated: C 10.83%, N 12.82%, S 9.78%. Found: C 10.98%, N 12.78%, S 9.57%.

EXAMPLE 35

Preparation of
2-imino-3-(4'-methoxy-2'-nitrophenyl)-thiazolidine hydrochloride

Into the suspension of 2.5 g (0.01 mole) of 4-methoxy-2-nitro-N-(2-thiocyanatoethyl)-aniline in 60 ml of anhydrous ethanol, dry gaseous hydrogen chloride is introduced for 1 hour under reflux. On cooling the crystals separated are filtered, washed with ether and dried.

2.1 g (73%) of the title compound are obtained in the form of yellowish white crystal powder. M.p.: 288°–290° C. (dimethyl formamide-ether).

Analysis for $C_{10}H_{12}ClN_3O_3S$ (Mw.: 289.8). Calculated: Cl 12.25%, N 14.50%, S 11.06%. Found: Cl 12.43%, N 14.23%, S 10.91%.

The corresponding base deliberated by means of 40 percent aqueous sodium hydroxide consists of a red crystal powder. M.p.: 108°–110° C. (ethyl acetate-petroleum ether).

EXAMPLE 36

Preparation of
2-imino-3-(4'-methoxy-2'-nitrophenyl)-thiazolidine hydrochloride

A mixture of 3 g (0.02 moles) of 4-methoxy-2-nitroaniline and 3.5 g (0.021 moles) of 2-bromoethyl rhodanide is stirred for 4 hours on an oil bath of 140° C. The melt becomes crystalline after about 3 hours. The crystals are treated with ether, filtered, washed with ether and dried.

5.0 g (75%) of the title compound are obtained in the form of red crystal powder. M.p.: 290° C. (dimethyl formamide-ether).

Analysis for $C_{10}H_{12}BrN_3O_3S$ (Mw.: 334.2). Calculated: Br 23.91%, N 12.57%, S 9.59%. Found: Br 23.86%, N 12.42%, S 9.45%.

Deliberation of the Base

The corresponding base is deliberated from the hydrochloride prepared above by means of 40 percent aqueous sodium hydroxide. A red crystal powder is obtained. M.p.: 108°–110° C. (ethyl acetate-petroleum ether).

The bases obtained in Examples 35 and 36 are identical on the basis of their melting points.

EXAMPLE 37

Preparation of
2-imino-3-(4'-chloro-2'-nitrophenyl)-thiazolidine hydrochloride

Into a suspension of 5.15 g (0.02 moles) of 4-chloro-2-nitro-N-(2-thiocyanatoethyl)-aniline in 50 ml of anhydrous ethanol dry hydrogen chloride is introduced for 1 hour under reflux. During the reaction the crystal mass turns from orange to pale yellow. On cooling the crystals are filtered, washed with ether and dried.

Thus, 5.5 g (93%) of the title compound are obtained. M.p.: 295°–296° C. (dec.) (ethanol)

Analysis for $C_9H_9Cl_2N_3O_2S$ (Mw.: 295.0). Calculated: Cl 24.04%, N 14.24%, S 10.87%. Found: Cl 24.08%, N 13.88%, S 10.61%.

EXAMPLE 38

Preparation of
2-imino-3-(5'-chloro-2'-nitrophenyl)-thiazolidine hydrochloride

Into a suspension of 11.5 g (0.045 moles) of 5-chloro-2-nitro-N-(2-thiocyanatoethyl)-aniline in 100 ml of anhydrous ethanol, dry gaseous hydrogen chloride is introduced for 30 minutes under reflux. The reaction mixture is evaporated to about the half of its volume in vacuo. On cooling the crystals are filtered, washed with ether and dried.

11 g (83%) of the title compound are obtained in the form of a pale yellow crystal powder. M.p.: 279°–281° C. (dec.) (methanol-ether).

Analysis for $C_9H_9Cl_2N_3O_2S$ (Mw.: 295.0). Calculated: Cl 24.04%, N 14.24%, S 10.87%. Found: Cl 23.92%, N 14.43%, S 11.20%.

EXAMPLE 39

Preparation of 2-imino-3-(4'-nitrophenyl)-thiazolidine 0.8 g (0.008 moles) of 2-aminothiazole and 0.56 g (0.004 moles) of 1-fluoro-4-nitrobenzene in 10 ml of anhydrous dimethyl sulfoxide are stirred at 80° C. for 3 hours, then the solution is poured into 50 ml of water and extracted 3 times with 20 ml of dichloromethane each time. The organic solutions are combined, dried over anhydrous magnesium sulfate, and evaporated under reduced pressure. The residue is treated with ether, filtered, washed with petroleum ether and dried.

0.35 g (40%) of the title compound are obtained. M.p.: 166° C. (ethyl acetate-petroleum ether).

The product is identical with the compounds prepared in Examples 56 and 40 on the basis of melting point, infrared spectra and thin-layer chromatography.

TLC (toluene-ethyl acetate 1:1) $R_f=0.25$.

EXAMPLE 40

Preparation of 2-imino-3-(4'-nitrophenyl)-thiazolidine

To 2 ml of fuming nitric acid (specific gravity: 1.52 g/cm$^3$) 1.8 g (0.01 mole) of 3-phenyl-2-imino-thiazolidine in 30 ml of chloroform are added drop by drop at 0° C. in 30 minutes. The reaction mixture is stirred for another 1 hour at the above temperature, then poured to 50 g of ice. The phases are separated, the aqueous phase is extracted twice with 50 ml of chloroform each time, the organic solutions are combined, washed 3 times with 20 ml of water each time, then dried over anhydrous magnesium sulfate, and evaporated under reduced pressure. The residue is crystallized from a mixture of ethyl acetate and petrol ether.

Thus, 1.5 g (67%) of the title compound are obtained in the form of yellow crystal powder. M.p.: 166° C. (ethyl acetate-petroleum ether).

Analysis for $C_9H_9N_3O_2S$ (Mw.: 223.2). Calculated: C 48.39%, H 4.03%, N 18.82%, S 14.37%. Found: C 48.59%, H 4.26%, N 18.67, S 14.41%.

EXAMPLE 41

Preparation of
2-imino-3-(4'-methoxycarbonyl-2',6'-dinitrophenyl)-thiazolidine 13 g (0.05 moles) of methyl 4-chloro-2,6-dinitrobenzoate in 200 ml of anhydrous dichloromethane are stirred with 10.2 g (0.1 mole) of 2-amino-thiazolidine at room temperature until no dinitro compound can be detected (TLC: petroleum ether-ethyl acetate 2:1). The reaction is finished in about 3 hours. The solution is extracted 3 times with 25 ml of water each time, then dried over anhydrous magnesium sulfate, and evaporated. The residue is treated with ether, filtered, washed with ether and dried.

In this way, 14.6 g (90%) of the title compound are obtained in the form of yellow crystal powder. M.p.: 138° C. (ethyl acetate-petroleum ether).

Analysis for $C_{11}H_{10}N_4O_6S$ (Mw.: 326.3). Calculated: C 40.49%, H 3.09, N 17.17%, S 9.83%. Found: C 40.21%, H 3.21, N 16.98%, S 10.14%.

EXAMPLE 42

Preparation of 3-phenyl-2-imino-thiazolidine hydrobromide 19.5 g (0.12 moles) of 2-bromoethyl rhodanide and 11 ml (0.12 moles) of aniline are refluxed in 30 ml of butanol for 3 hours. On cooling the crystals separated are filtered, washed with acetone, then with ether and dried.

26 g (85%) of the title compound are obtained in the form of colorless needles. M.p.: 219° C. (ethanol).

Analysis for $C_9H_{11}BrN_2S$ (Mw.: 259.2). Calculated: C 41.71%, H 4.27%, N 10.81%, S 12.37%. Found: C 41.69%, H 4.47%, N 10.84%, S 12.46%.

EXAMPLE 43

Preparation of
2-imino-3-(3'-hydroxy-4'-carboxyphenyl)-thiazolidine hydrobromide A mixture of 15.3 g (0.1 mole) of 4-amino-2-hydroxybenzoic acid, 18.5 g (0.11 moles) of 2-bromoethyl rhodanide, 8.0 ml (0.1 mole) of pyridine and 140 ml of n-butanol is heated under reflux for 10 hours. The mixture is evaporated under reduced pressure, the residue is treated with 50 ml of ethanol, filtered, washed with some ethanol, then with acetone and dried.

In this way 14.1 g (44%) of the title compound are obtained in the form of colorless crystal powder. M.p.: 237°–239° C. (methanol-acetone).

Analysis for $C_{10}H_{11}BrN_2O_3S$ (Mw.: 319.2). Calculated: C 37.63%, H 3.47%, Br 25.03%, N 8.78%, S 10.05%. Found: C 37.87%, H 3.51%, Br 25.14%, N 8.51%, S 10.40%.

TLC (5 percent aqueous sodium chloride solution-ethanol 2:18) $R_f=0.7$.

EXAMPLE 44

Preparation of
2-imino-3-(2'-methoxyphenyl)-thiazolidine
hydrobromide 12.3 g (0.1 mole) of 2-methoxyaniline are heated under reflux with 16.6 g (0.1 mole) of 2-bromoethyl rhodanide in 75 ml of n-butanol for 12 hours. On cooling the crystals formed are filtered, washed with some ethanol, then with acetone and dried.

20.5 g (71%) of the title compound are obtained in the form of colorless crystal powder. M.p.: 243°–245° C. (methanol-acetone).

Analysis for $C_{10}H_{13}BrN_2OS$ (Mw.: 289.2). Calculated: C 41.53%, H 4.53%, Br 27.63%, N 9.69%, S 11.09%. Found: C 41.77%, H 4.35%, Br 27.41%, N 9.82%, S 11.40%.

TLC (5 percent aqueous sodium chloride solution-ethanol 1:19) $R_f=0.6$.

EXAMPLE 45

Preparation of 2-imino-3-(4'-chlorophenyl)-thiazolidine hydrobromide 5 g (0.04 moles) of 4-chloroaniline and 6.7 g (0.04 moles) of 2-bromoethyl rhodanide in 15 ml of n-butanol are heated under reflux for 1 hour. On cooling the crystals are filtered, washed with ether and dried.

Thus, 9.5 g (81%) of the title compound are obtained in the form of colorless crystal powder. M.p.: 300° C. (dec.) (ethanol-ether).

Analysis for $C_9H_{10}BrClN_2S$ (Mw.: 293.6). Calculated: C 36.81%, H 3.43%, N 9.54%. Found: C 36.76%, H 3.63%, N 9.66%.

The hydrobromide obtained above is treated with 40 percent aqueous sodium hydroxide to give the corresponding base. M.p.: 74°–76° C. (ethyl acetate).

EXAMPLE 46

Preparation of 2-imino-3-(4'-bromophenyl)-thiazolidine hydrobromide 8.6 g (0.05 moles) of 4-bromoaniline and 8.3 g (0.05 moles) of 2-bromoethyl rhodanide in 30 ml of n-butanol are heated under reflux for 3 hours. On cooling the crystals formed are filtered, washed with ether and dried.

In this way 14 g (82%) of the title compound are obtained in the form of colorless crystal powder. M.p.: 306° C. (dec.) (methanol-ether).

Analysis for $C_9H_{10}BrN_2S$ (Mw.: 338.1). Calculated: C 31.97%, H 2.98%, N 8.28%. Found: C 31.79%, H 2.97%, N 8.08%.

The hydrobromide obtained above is treated with 40 percent aqueous sodium hydroxide to deliberate the corresponding base. M.p.: 58°–60° C. (benzene-petroleum ether).

EXAMPLE 47

Preparation of
2-imino-3-(4'-methoxyphenyl)-thiazolidine
hydrobromide 6.15 g (0.05 moles) of 4-methoxyaniline and 8.3 g (0.05 moles) of 2-bromoethyl rhodanide in 15 ml of n-butanol are heated under reflux for 1 hour. On cooling the crystals are filtered, washed with ether and dried.

12 g (83%) of the title compound are obtained in the form of colorless crystal powder. M.p.: 274° C. (methanol-ether).

Analysis for $C_{10}H_{13}BrN_2OS$ (Mw.: 289.2). Calculated: C 41.52%, H 4.53%, N 9.68%, S 11.09%. Found: C 41.67%, H 4.27%, N 9.39%, S 11.36%.

The hydrobromide obtained above is treated with 40 percent aqueous sodium hydroxide solution to deliberate the corresponding base. M.p.: 116° C. (ethyl acetate).

EXAMPLE 48

Preparation of
2-imino-3-(4'-chloro-3'-trifluoromethylphenyl)-thiazolidine hydrobromide A mixture of 1.95 g (0.01 mole) of 4-chloro-3-trifluoromethylaniline, 1.7 g (0.01 mole) of 2-bromoethyl rhodanide and 20 ml of n-butanol is heated under reflux for 6 hours. The solution is evaporated under reduced pressure, the crystalline residue is treated with acetone, filtered, washed with acetone and dried.

In this way 2.5 g (71%) of the title compound are obtained in the form of colorless crystal powder. M.p.: 328°–330° C. (dec.) (ethanol-ether)

Analysis for $C_9H_8BrClF_3N_2S$ (Mw.: 349.8). Calculated: Br 22.85%, N 8.01%, S 9.17%. Found: Br 22.48%, N 7.73%, S 8.64%.

EXAMPLE 49

Preparation of
4-chloro-N-(1-ethyl-2-mesyloxyethyl)-2-nitroaniline

To the solution of 12.2 g (0.05 moles) of N-(1-ethyl-2-hydroxyethyl)-4-chloro-2-nitroaniline in 20 ml of anhydrous pyridine 6.3 g (4.2 ml, 0.055 moles) of mesyl chloride are added, drop by drop at 0° C. The reaction mixture is stirred for another 3 hours, then poured into 100 ml of ice water, filtered, washed with water and dried.

Thus, 10.2 g (63%) of the title compound are obtained in the form of red crystal powder. M.p.: 91°–93° C. (methanol).

Analysis for $C_{11}H_{15}ClN_2O_5S$ (Mw.: 322.8). Calculated: Cl 10.99%, N 8.68%. Found: Cl 10.62%, N 8.47%.

EXAMPLE 50

Preparation of
4-chloro-2-nitro-N-(1-ethyl-2-thiocyanatoethyl)-aniline

A mixture of 6.5 g (0.02 moles) of 4-chloro-N-(1-ethyl-2-mesyloxyethyl)-2-nitroaniline, 2.9 g (0.03 moles) of potassium rhodanide and 100 ml of ethanol is heated under reflux for 6 hours. The mixture is poured into 300 ml of water, the crystals formed are filtered, washed with water and dried.

4.8 g (84%) of the title compound are obtained in the form of yellowish red crystal powder. M.p.: 126°–128° C. (methanol).

Analysis for $C_{11}H_{12}ClN_3O_2S$ (Mw.: 285.8). Calculated: Cl 12.42%, N 14.70%, S 11.22%. Found: Cl 12.10%, N 14.53%, S 11.25%.

EXAMPLE 51

Preparation of
4-ethyl-2-imino-3-(2'-amino-4'-chlorophenyl)-thiazolidine dihydrochloride 8.6 g (0.03 moles) of 4-chloro-2-nitro-N-(1-ethyl-2-thiocyanoethyl)-aniline are hydrogenated in the mixture of 50 ml of dichloromethane and 100 ml of methanol, in the presence of 1 g of palladium/carbon catalyst. The catalyst is removed by filtration, the filtrate is saturated with gaseous hydrogen chloride at 0° C., then evaporated under reduced pressure. The residue is crystallized from a mixture of methanol and ether.

4.2 g (63%) of the title compound are obtained. M.p.: 123°–125° C. (dec.) (methanol-ether).

Analysis for $C_{11}H_{16}Cl_3N_3S$ (Mw.: 328.7). Calculated: C 40.19%, H 4.90%, N 12.78%, S 9.76%. Found: C 39.94%, H 4.71%, N 13.03%, S 10.13%.

EXAMPLE 52

Preparation of
2-imino-5-methyl-3-(4'-chloro-2'-nitrophenyl)-thiazolidine hydrochloride 12 g (0.044 moles) of 4-chloro-2-nitro-N-(2-methyl-2-thiocyanatoethyl)-aniline are suspended in 150 ml of anhydrous ethanol and dry gaseous hydrogen chloride is introduced into the suspension under reflux for 2 hours. After 30 minutes a homogenous solution is obtained, then crystals develop. On cooling the crystals are filtered, washed with ethanol, then with ether and dried.

11.5 g (85%) of the title compound are obtained in the form of pale yellow crystal powder. M.p.: 281°–283° C. (ethanol).

Analysis for $C_{10}H_{11}Cl_2N_3O_2S$ (Mw.: 308.3). Calculated: C 38.96%, H 3.59%, S 10.40%. Found: C 38.75%, H 3.30%, S 10.72%.

EXAMPLE 53

Preparation of
2-imino-5-methyl-3-(2'-amino-4'-chlorophenyl)-thiazolidine di(ethanesulfonate)

5 g (0.018 moles) of 4-chloro-2-nitro-N-(2-methyl-2-thiocyanatoethyl)-aniline are hydrogenated in the mixture of 100 ml of methanol and 50 ml of chloroform, in the presence of 0.5 g of palladium/carbon catalyst. The mixture is cooled to 0° C., the catalyst is removed by filtration. To the filtrate 3.13 ml (4.23 g, 0.038 moles) of ethanesulfonic acid are added and the mixture is left to stand at the above temperature, then evaporated in vacuo. The residue is recrystallized from a mixture of methanol and ether.

3 g (35%) of the title compound are obtained in the form of colorless needles. M.p.: 141°–143° C. (methanol-ether).

Analysis for $C_{14}H_{24}ClN_3O_6S_3$ (Mw.: 462.0). Calculated: C 36.39% H 5.23%, Cl 7.67%, S 20.82%. Found: C 36.28%, H 5.36%, Cl 7.86%, S 20.80%.

EXAMPLE 54

Preparation of
N-(1-ethyl-2-hydroxyethyl)-4-chloro-2-nitroaniline 38.4 g (0.2 moles) of 2,5-dichloro-nitrobenzene are heated under reflux with 20 ml (0.22 moles) of (±) 2-amino-1-butanol in 100 ml of pyridine for 5 hours. The reaction mixture is evaporated in vacuo, the oily residue is rubbed with water to induce crystallization. The crystals are filtered, dried and recrystallized from ether.

36 g (73%) of the title compound are obtained in the form of orange-red needles. M.p.: 45° C. (ether).

Analysis for $C_{20}H_{13}ClN_2O_3$ (Mw.: 244.7). Calculated: C 49.07%, H 5.35%, H 11.44%. Found: C 49.11%, H 5.32%, H 11.55%.

EXAMPLE 55

Preparation of
2-imino-3-(2'-amino-4'-chlorophenyl)-thiazolidine dihydrochloride A mixture of 2.6 g (0.01 mole) of 2-imino-3-(4'-chloro-2'-nitrophenyl)-thiazolidine and 11.3 g (0.05 moles) of stannous chloride dihydrate in ethanol is heated under inert gas to 70° C. The reaction proceeds in about 30 minutes as indicated by a color change of the solution. The mixture is poured into about 200 ml of water, the ethanol is removed under reduced pressure, and the residue is adjusted to pH=9 with 10 percent aqueous sodium hydroxide. The solution is extracted three times with chloroform, using 50 ml of chloroform each time. The combined organic phases are washed with water, dried over anhydrous magnesium sulfate and evaporated in vacuo. The residue is dissolved in methanol, saturated with hydrogen chloride and the crystal formation is induced by the addition of ether.

In this way 1.2 g (40%) of the title compound are obtained in the form of colorless crystal powder. M.p.: 185°–186° C. (dec.) (methanol-ether).

EXAMPLE 56

Preparation of 2-imino-3-(4'-nitrophenyl)-thiazolidine

A mixture of 1 g (0.0038 moles) of 1-(4-nitrophenyl)-thiourea [Dyson, G. M. and George, H. H., J. Chem. Soc., 125, 1703–7 (1924)], 10 ml of dibromoethane and 10 ml of dimethyl formamide is stirred at 140° C. for 2 hours. The solution is cooled, the crystals formed are filtered, washed with acetone, and dried.

0.4 g (35%) of the hydrobromide of the title compound are obtained. M.p.: 276°–278° C. (ethanol-ether).

From the hydrobromide prepared above, 0.27 g (95%) of the title compound are deliberated. M.p.: 166° C. (ethyl acetate-petroleum ether).

EXAMPLE 57

Preparation of 3-(4-nitrophenyl)-2-iminothiazolidine (a) N-(2-Mesyloxyethyl)-4-nitroaniline 3.6 g (0.02 moles) of N-(2-hydroxyethyl)-4-nitroaniline [Belgian patent specification No. 639 251; C.A., 63, 4427d (1965)] are dissolved in 11 ml of pyridine, and to the solution obtained 1.86 ml (0.024 moles) of methanesulfonyl chloride are added drop by drop at 0° C. The reaction mixture is stirred for another 4 hours at the above temperature, then poured into 100 ml of ice water. The crystals formed are filtered, washed with water and dried.

3.4 g of N-(2-mesyloxyethyl)-4-nitroaniline are obtained in the form of red-brown crystals. M.p.: 136°–138° C. (ethyl acetate)

Analysis for $C_9H_{12}N_2O_5S$. Calculated: C 41.53%, H 4.65%, N 10.76%, S 12.32%. Found: C 41.31%, H 4.54%, N 10.49%, S 12.41%.

(b) S-[2-(4-nitroanilino)-ethyl]-isothiuronium mesylate

A mixture of 2.0 g (0.008 moles) of N-(2-mesyloxyethyl)-4-nitroaniline, 1.2 g (0.016 moles) of thiourea and 20 ml of ethanol is heated under reflux for 6 hours. To the solution obtained 30 ml of ethyl acetate are added, then the mixture is cooled. The crystals formed are filtered, washed with ethyl acetate and dried.

Thus, 2.2 g (85%) of S-[2-(4-nitroanilino)-ethyl]-isothiuronium mesylate are obtained in the form of yellow crystals. M.p.: 169°–171° C. (methanol-ethyl acetate).

Analysis for $C_{10}H_{16}N_4O_5S$. Calculated: C 35.71%, H 4.79%, N 16.66%, S 19.06%. Found: C 35.67%, H 4.61%, N 16.80%, S 19.02%.

(c) 3-(4-Nitrophenyl)-2-iminothiazolidine

A mixture of 1.0 g (0.003 moles) of S-[2-(4-nitroanilino)-ethyl]-isothiuronium mesylate and 50 ml of distilled water is heated under reflux for 10 hours under inert gas. On cooling 5 g of sodium carbonate are added to the solution and the latter is extracted with 3×50 ml of dichloromethane. The organic phases are combined, dried over anhydrous magnesium sulfate and evaporated under reduced pressure. The residue is purified by chromatography (ethyl acetate-hexane 1:1; $R_f$=0.25).

0.08 g (12%) of the title compound are obtained. M.p.: 165°–166° C. (ethyl acetate-petroleum ether).

EXAMPLE 58

Preparation of
2-imino-3-(2'-chloro-6'-nitrophenyl)-thiazolidine hydrochloride (a) 19.5 g (0.09 moles) of 2-(2-chloro-6-nitroanilino)-ethanol are dissolved in 60 ml of pyridine and to the solution obtained 9.7 ml (0.12 moles) of methanesulfonyl chloride are added drop by drop. During the addition the temperature of the mixture is kept under 5° C. by means of ice cooling. The mixture is stirred for 2 hours, then poured into 300 ml of ice water. The red oil formed is separated, the aqueous solution is extracted with 3×30 ml of dichloromethane, the organic phases are combined, dried over anhydrous magnesium sulfate and evaporated in vacuo.

21.0 g (93%) of 2-chloro-N-(2-mesyloxyethyl)-6-nitroaniline are obtained in the form of red oil.

Analysis for $C_9H_{11}ClN_2O_5S$. Calculated: N 9.51%, S 10.88%. Found: N 9.28%, S 11.19%.

(b) A mixture consisting of 25 g (0.1 mole) of 2-chloro-N-(2-mesyloxyethyl)-6-nitroaniline, 16 g (0.16 moles) of potassium rhodanide and 300 ml of ethanol is stirred for 12 hours under reflux. The mixture is concentrated under reduced pressure and the residue is poured into 500 ml of water. On cooling the crystals are filtered, washed with water and dried.

In this way 20.5 g (79.5%) of 2-chloro-6-nitro-N-(2-thiocyanatoethyl)-aniline are obtained in the form of orange-red crystal powder. M.p.: 92°–94° C. (ethanol).

Analysis for $C_9H_8ClN_3O_2S$. Calculated: Cl 13.77%, N 16.30%, S 12.40%. Found: Cl 13.88%, N 16.51%, S 12.87%.

(c) 3 g (0.0117 moles) of 2-chloro-6-nitro-N-(2-thiocyanatoethyl)-aniline are suspended in 50 ml of ethanol and the suspension obtained is saturated with gaseous hydrogen chloride under reflux. The solvent is evaporated, the crystalline residue is treated with ether, filtered, washed with ether and dried.

Thus, 2.9 g (84%) of the title compound are obtained in the form of pale yellow crystal powder. M.p.: 279°–280° C. (ethanol-ether).

Analysis for $C_9H_9Cl_2N_3O_2S$. Calculated: Cl 24.04%, N 14.24%, S 10.87%. Found: Cl 23.57%, N 14.17%, S 10.98%.

EXAMPLE 59

Preparation of
2-imino-3-(2'-amino-6'-chlorophenyl)-thiazolidine ethanesulfonate 2.95 g (0.0117 moles) of 2-chloro-6-nitro-N-(2-thiocyanatoethyl)-aniline are hydrogenated in a mixture of 50 ml of methanol and 50 ml of dichloromethane, in the presence of 0.3 g of palladium/carbon catalyst. From the mixture cooled to 0° C. the catalyst is removed by filtration, and 3.3 g (2.5 ml, 0.03 moles) of ethanesulfonic acid are added to the filtrate. The mixture obtained is stirred for 2 hours at the above temperature, then evaporated under reduced pressure. The residue is treated with acetone, filtered, washed with acetone and dried.

2.5 g (63%) of the title compound are obtained in the form of colorless crystals. M.p.: 168°–170° C. (methanol-ether).

Analysis for $C_{11}H_{18}ClN_3O_3S_2$. Calculated: Cl 10.47%, N 12.39%, S 18.88%. Found: Cl 10.12%, N 12.40%, S 19.11%.

EXAMPLE 60

Preparation of
2-chloro-4-nitro-N-(2-thiocyanatoethyl)-aniline (a) To the solution of 7.1 g (0.033 moles) of 2-(2-chloro-4-nitroanilino)-ethanol in 20 ml of pyridine 3.6 ml (0.044 moles) of methanesulfonyl chloride are added drop by drop under ice cooling. The reaction mixture is stirred for 1 hour, then poured into 100 ml of ice water. The crystals formed are filtered, washed with water and dried.

7.0 g (72%) of 2-chloro-N-(2-mesyloxyethyl)-4-nitroaniline are obtained in the form of yellow crystals. M.p. 114°–115° C. (ethanol).

Analysis for $C_9H_{11}ClN_2O_5S$. Calculated: Cl 12.04%, N 9.51%, S 10.88%. Found: Cl 11.89%, N 9.72%, S 10.54%.

(b) 7 g (0.0237 moles) of 2-chloro-N-(2-mesyloxyethyl)-4-nitroaniline and 3.7 g (0.038 moles) of potassium rhodanide in 150 ml of ethanol are stirred for 12 hours under reflux. The mixture is poured into 150 ml of water, the crystals formed are filtered, washed with water and dried.

6.0 g (98%) of the title compound are obtained in the form of yellow crystals. M.p.: 148°–150° C. (dimethyl formamide).

Analysis for $C_9H_8ClN_3O_2S$. Calculated: Cl 13.77%, S 12.40%. Found: Cl 13.54%, S 12.12%.

EXAMPLE 61

Preparation of
2-imino-3-(2'-chloro-4'-nitrophenyl)-thiazolidine hydrochloride 6 g (0.0234 moles) of 2-chloro-4-nitro-N-(2-thiocyanatoethyl)-aniline are suspended in 100 ml of ethanol and the suspension obtained is saturated with gaseous hydrogen chloride for about 1 hour under boiling.

On cooling the crystals are filtered, washed with ether and dried.

5.6 g (82%) of the title compound are obtained in the form of yellow crystals. M.p.: 194°–196° C. (ethanol).

Analysis for $C_9H_9Cl_2N_3O_2S$. Calculated: Cl 24.04%, N 14.24%, S 10.87%. Found: Cl 24.27%, N 14.30%, S 11.02%.

EXAMPLE 62

Preparation of 2,4,6-trinitro-N-(2-thiocyanatoethyl)-aniline (a) 6 g (0.022 moles) of N-(2-hydroxyethyl)-2,4,6-trinitroaniline [Waldtötter, K. F., Rec. Trav. Chim., 57, 1294 (1938)] are dissolved in 18 ml of pyridine, and to the solution obtained 2.4 ml (0.031 moles) of methane sulfonyl chloride are added drop by drop under ice cooling. The reaction mixture is stirred for 2 hours, then poured into 200 ml of ice water. The crystals formed are filtered, washed with water and dried.

5.5 g (71%) of N-(2-mesyloxyethyl)-2,4,6-trinitroaniline are obtained in the form of orange crystals. M.p.: 121°–123° C. (ethyl acetate).

Analysis for $C_9H_{10}N_4O_9S$. Calculated: C 30.86%, H 2.88%, N 16.00%, S 9.15%. Found: C 30.90%, H 2.71%, N 15.92%, S 9.21%.

(b) A mixture of 5 g (0.014 moles) of N-(2-mesyloxyethyl)-2,4,6-trinitroaniline, 4 g (0.04 moles) of potassium rhodanide and 50 ml of anhydrous dimethyl formamide is stirred for 1.5 hours at 110° C. The reaction mixture is poured into ice water, the crystals formed are filtered, washed thoroughly with water and dried.

3.8 g (87%) of the title compound are obtained in the form of orange-red crystals. M.p.: 124°–126° C. (ethyl acetate).

Analysis for $C_9H_7N_5O_6S$. Calculated: C 34.51%, H 2.25%, N 22.36%, S 10.24%. Found: C 34.34%, H 2.50%, N 21.94%, S 10.35%.

EXAMPLE 63

Preparation of 2-imino-3-(2',4',6'-trinitrophenyl)-thiazolidine

Dry gaseous hydrogen chloride is introduced into 1.2 g (0.0038 moles) of 2,4,6-trinitro-N-(2-thiocyanatoethyl)-aniline in 120 ml of anhydrous ethanol for 5 hours, while the mixture is heated under reflux. The solvent is distilled off, the residue is boiled with 30 ml of ethyl acetate for 10 minutes, then the warm mixture is filtered. The insoluble matter is shaken with 30 ml of ethyl acetate and 20 ml of 10 percent aqueous sodium carbonate solution. The phases are separated, and the aqueous solution is extracted twice with 10 ml of ethyl acetate each time. The organic phases are combined, dried over anhydrous magnesium carbonate and evaporated. In this way 0.084 g (7%) of the title compound are obtained. M.p.: 160°–162° C. (ethyl acetate).

EXAMPLE 64

Preparation of 2-imino-3-(2',4',6'-trinitrophenyl)-thiazolidine

To the solution of 11.5 g (0.113 moles) of 2-aminothiazolidine in 225 ml of anhydrous ethyl acetate 12.5 g (0.05 moles) of 2,4,6-trinitro-chlorobenzene in 150 ml of anhydrous ethyl acetate are added drop by drop at room temperature. After 2 hours 600 ml of ethyl acetate and 800 ml of 10 percent sodium carbonate solution are added and the reaction mixture is well shaken. The phases are separated, the aqueous phase is extracted twice with 100 ml of ethyl acetate each time, the organic phases are combined, dried over anhydrous magnesium sulfate, then evaporated.

In this way 13.8 g (88%) of the title compound are obtained. M.p.: 160°–162° C. (ethyl acetate).

Analysis for $C_9H_7N_5O_6S$. Calculated: C 34.51%, H 2.25%, N 22.36%, S 10.23%. Found: C 34.35%, H 2.08%, N 21.90%, S 10.38%.

EXAMPLE 65

Preparation of bis[2-(4-chloro-2-nitroanilino)-ethyl]disulfide (a) A mixture of 3.8 g (0.02 moles) of 2,5-dichloronitrobenzene, 2.3 g (0.02 moles) of 2-aminoethanethiol hydrochloride, 6 ml of triethyl amine and 25 ml of ethanol is heated under reflux for 10 hours. On cooling the crystals formed are filtered, washed with cold methanol and dried.

3.2 g of 4-chloro-2-nitro-N-(2-thiocyanatoethyl)-aniline are obtained. M.p.: 187°–188° C. (dioxane).

Analysis for $C_{16}H_{16}Cl_2N_4O_4S_2$. Calculated: C 41.47%, H 3.48%, S 13.84%. Found: C 41.53%, H 3.36, S 13.56%.

(b) 2.6 g (0.01 mole) 4-chloro-2-nitro-N-(2-thiocyanatoethyl)-aniline are heated with a solution of 0.3 g of metallic sodium in 30 ml of anhydrous ethanol for 10 minutes under reflux. On cooling the crystals are filtered, washed with ether and dried.

2 g (86%) of the title compound are obtained. M.p.: 187°–188° C. (dioxane or dimethyl formamide).

EXAMPLE 66

Preparation of 2-imino-3-(4'-chloro-2'-nitrophenyl)-thiazolidine hydrobromide 1 g (0.0022 moles) of bis[2-(4-chloro-2-nitroanilino)ethyl]disulfide and 0.8 g (0.0075 moles) of cyanogen bromide dissolved in 30 ml of dioxane are heated under reflux for 4 hours. The crystals formed are separated from the cold mixture, washed with dioxane and ether, then dried.

1.2 g (81%) of the title compound are obtained in the form of yellow crystals. M.p.: 335°–336° C. (ethanol).

EXAMPLE 67

Preparation of 4-acetylamino-N-(2-thiocyanatoethyl)-2-nitroaniline (a) A solution of 27.7 g (0.14 moles) of 4-acetylamino-2-nitrofluorobenzene [Swarts, Rec. Trav. Chim., 35, 141] and 17.8 ml (0.29 moles) of 2-aminoethanol in 300 ml of n-butanol is heated under reflux for 2.5 hours, then evaporated in vacuo. The residue is treated with water, filtered and washed with water.

In this way 33 g (98%) of 4-acetylamino-N-(2-hydroxyethyl)-2-nitroaniline are obtained in the form of yellow crystals. M.p.: 186° C. (nitromethane).

Analysis for $C_{10}H_{13}N_3O_4$. Calculated: C 50.20%, H 5.48%, N 17.57%. Found: C 49.92%, H 5.25%, N 17.69%.

(b) 33.5 g (0.14 moles) of 4-acetylamino-N-(2-hydroxyethyl)-2-nitroaniline are dissolved in 200 ml of anhydrous pyridine and to the solution obtained 14.1 ml (0.18 moles) of methanesulfonyl chloride are added drop by drop under ice cooling. The reaction mixture is stirred for 3 hours, then poured into 1.5 liters of ice water. The crystals are filtered, washed with alcohol, then with ether and dried.

41.4 g (93%) of 4-acetylamino-N-(2-mesyloxyethyl)-2-nitroaniline are obtained in the form of yellow crystals. M.p.: 166° C. (dioxane).

Analysis for $C_{11}H_{15}N_3O_6S$. Calculated: N 13.24%, S 10.11%. Found: N 13.09%, S 10.37%.

(c) A solution of 41.4 g (0.13 moles) of 4-acetylamino-N-(2-mesyloxyethyl)-2-nitroaniline and 25.4 g (0.26 moles) of potassium rhodanide in a mixture of 350 ml of anhydrous dioxane and 300 ml of anhydrous ethanol is heated under reflux for 14 hours, then the solvent is removed under reduced pressure. The crystalline residue is treated with water, filtered, washed with water and dried.

Thus, 33.8 g (93%) of the title compound are obtained in the form of yellow crystals. M.p.: 168° C. (dioxane)

Analysis for $C_{11}H_{12}N_4O_3S$. Calculated: C 47.14%, H 4.32%, N 19.99%, S 11.44%. Found: C 46.94%, H 4.58%, N 20.20%, S 11.30%.

EXAMPLE 68

Preparation of 2-imino-3-(4′-amino-2′-nitrophenyl)-thiazolidine 1.4 g (0.005 moles) of 4-acetylamino-N-(2-isothiocyanatoethyl)-2-nitroaniline are dissolved in the mixture of 80 ml of anhydrous methanol and 20 ml of dioxane, and the mixture is heated under reflux for 10 hours, while dry gaseous hydrogen chloride is introduced. Then the solution is evaporated, the residue is dissolved in some water, diluted with 5 percent aqueous sodium carbonate until pH=9 and extracted with ethyl acetate. The organic solution is dried over anhydrous magnesium sulfate and evaporated to yield 50 g of red oil which is purified by chromatography. The impurities are removed by eluting the column with a mixture of dichloromethane and acetone in a ratio of 10 to 1, then the product is eluted with acetone.

In this way 0.8 g (65%) of the title compound are obtained. M.p.: 138°–139° C. (ethyl acetate).

Analysis for $C_9H_{10}N_4O_2S$. Calculated: C 45.37%, H 4.23%, N 23.52%, S 13.46%. Found: C 45.56%, H 4.25%, N 23.77%, S 13.33%.

What we claim is:

1. A compound of the Formula (I)

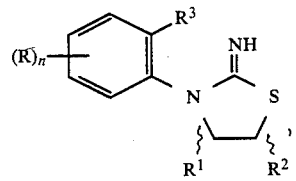

wherein
$R^1$ and $R^2$ are each hydrogen or lower alkyl;
$R^3$ is nitro or amino;
R is halo, lower alkyl, nitro, amino, hydroxy, lower alkoxy, carboxy, lower alkoxycarbonyl, or $C_1$ to $C_2$ haloalkyl having 1, 2, or 3 halo atoms; and
n is 0, 1 or 2, or a pharmaceutically acceptable acid addition salt thereof.

2. A compound of the Formula (I)

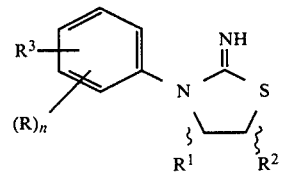

wherein
$R^1$ and $R^2$ are each hydrogen;
$R^3$ is nitro;
R is chloro, trifluoromethyl, methoxy, or amino; and
n is 0 or 1, or a pharmaceutically acceptable acid addition salt thereof.

3. A compound of the Formula (Ib)

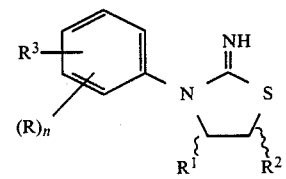

wherein
$R^1$ and $R^2$ are each hydrogen or methyl;
$R^3$ is amino;
R is chloro, trifluoromethyl, methoxy or amino; and
n is 0 or 1, or a pharmaceutically acceptable acid addition salt thereof.

4. 3-(2-Amino-4-chlorophenyl)-2-iminothiazolidine or a pharmaceutically acceptable acid addition salt thereof as defined in claim 3.

5. 3-(2-Amino-4-chlorophenyl)-2-imino-5-methyl-thiazolidine or 3-(2-amino-4-methylphenyl)-2-iminothiazolidine or a pharmaceutically acceptable acid addition salt thereof as defined in claim 3.

6. An antidepressant pharmaceutical composition which comprises as active ingredient a therapeutically effective amount of the compound of the Formula (I) as defined in claim 1 or a pharmaceutically acceptable acid addition salt thereof in combination with a pharmaceutically acceptable inert carrier.

7. An antidepressant pharmaceutical composition which comprises as active ingredient a therapeutically effective amount of the compound of the Formula (I) as defined in claim 2 or a pharmaceutically acceptable acid addition salt thereof in combination with a pharmaceutically acceptable inert carrier.

8. An antidepressant pharmaceutical composition which comprises as active ingredient a therapeutically effective amount of the compound of the Formula (I) as defined in claim 3 or a pharmaceutically acceptable acid addition salt thereof in combination with a pharmaceutically acceptable inert carrier.

* * * * *